(12) United States Patent
Patkar et al.

(10) Patent No.: US 9,688,657 B2
(45) Date of Patent: Jun. 27, 2017

(54) SYNTHESIS OF DABIGATRAN

(71) Applicant: USV Private Limited, Mumbai (IN)

(72) Inventors: Laxmikant Narhari Patkar, Mumbai (IN); Harish Kashinath Mondkar, Mumbai (IN); Nitin Dnyaneshwar Arote, Mumbai (IN); Sachin Shivaji Patil, Mumbai (IN); Tanaji Shamrao Jadhav, Mumbai (IN); Nitin Nivrutti Hagavane, Mumbai (IN); Rajesh Ganpat Bhopalkar, Mumbai (IN)

(73) Assignee: USV Private Limited, Mumbai Maharashtra (IN)

( * ) Notice: Subject to any disclaimer, the term of this patent is extended or adjusted under 35 U.S.C. 154(b) by 0 days.

(21) Appl. No.: 14/779,911

(22) PCT Filed: Mar. 25, 2014

(86) PCT No.: PCT/IN2014/000188
§ 371 (c)(1),
(2) Date: Sep. 24, 2015

(87) PCT Pub. No.: WO2014/167577
PCT Pub. Date: Oct. 16, 2014

(65) Prior Publication Data
US 2016/0060248 A1   Mar. 3, 2016

(30) Foreign Application Priority Data

Mar. 25, 2013 (IN) .......................... 1117/MUM/2013
Jun. 6, 2013 (IN) .......................... 1957/MUM/2013

(51) Int. Cl.
*C07C 271/20*   (2006.01)
*C07D 401/12*   (2006.01)

(52) U.S. Cl.
CPC .......... *C07D 401/12* (2013.01); *C07C 271/20* (2013.01)

(58) Field of Classification Search
CPC ........................... C07D 401/12; C07C 271/20
(Continued)

(56) References Cited

U.S. PATENT DOCUMENTS 4,322,431 A * 3/1982 Habicht ............... C07D 235/12
514/394
2011/0275824 A1* 11/2011 Gnad .................... C07C 271/64
546/273.4

FOREIGN PATENT DOCUMENTS

CN    102633713    *  8/2012
CN    102850326    *  1/2013
(Continued)

OTHER PUBLICATIONS

Chen; Heterocycles 2013, 87, 1699-1710. Abstract. Published online Jun. 27, 2013.*
(Continued)

*Primary Examiner* — Noble Jarrell
*Assistant Examiner* — Daniel Carcanague
(74) *Attorney, Agent, or Firm* — Schwegman Lundberg & Woessner, P.A

(57) ABSTRACT

The present invention relates to a process for preparation of Dabigatran etexilate or pharmaceutically acceptable salt thereof. The present invention relates to novel compounds, in particular Ethyl-3-{[(2-formyl-1-methyl-1H-benzimidazole-5-yl)carbonyl]-(2-pyridinyl) amino}propanoate and Ethyl-3-{[(2-dichloromethyl-1-methyl-1H-benzimidazole-5-yl)carbonyl]-(2-pyridinyl)amino}propanoate and process for preparation thereof. The present invention further relates
(Continued)

to the use of these novel compounds in the preparation of Dabigatran etexilate or pharmaceutically acceptable salt thereof.

24 Claims, 4 Drawing Sheets

(58) Field of Classification Search
USPC .................................................... 546/273.4
See application file for complete search history.

(56) References Cited

FOREIGN PATENT DOCUMENTS

| CN | 102850327 | * | 1/2013 |
|----|-----------|---|--------|
| WO | WO-2012004397 A1 | | 1/2012 |
| WO | WO-2012077136 A2 | | 6/2012 |
| WO | WO2015027893 | * | 3/2015 |

OTHER PUBLICATIONS

International Application No. PCT/IN2014/000188, International Search Report and Written Opinion, mailed Feb. 11, 2015, 15 pgs.

* cited by examiner

SYNTHESIS OF DABIGATRAN

RELATED APPLICATION

This application is a U.S. National Stage Filing under 35 U.S.C. §371 from International Application No. PCT/IN2014/000188, filed on Mar. 25, 2014, and published as WO 2014/167577 on Oct. 16, 2014, which claims the benefit of priority under 35 U.S.C. §119 to Indian Provisional Applications, 1117/MUM/2013 dated 25 Mar. 2013 and 1957/MUM/2013 dated 6 Jun. 2013, all of which applications and publication are hereby incorporated by reference herein in their entireties.

FIELD OF INVENTION

The present invention relates to a process for preparation of Dabigatran etexilate or pharmaceutically acceptable salt thereof. The present invention relates to novel compounds, in particular Ethyl-3-{[(2-formyl-1-methyl-1H-benzimidazole-5-yl)carbonyl]-(2-pyridinyl)amino}propanoate and Ethyl-3-{[(2-dichloromethyl-1-methyl-1H-benzimidazole-5-yl)carbonyl]-(2-pyridinyl)amino}propanoate and process for preparation thereof. The present invention further relates to the use of these novel compounds in the preparation of Dabigatran etexilate or pharmaceutically acceptable salt thereof.

BACKGROUND OF THE INVENTION

Dabigatran etexilate mesylate is a direct thrombin inhibitor, with the chemical name, β-Alanine, N-[[2-[[[4-[[[(hexyloxy)carbonyl]amino]iminomethyl]phenyl]amino]methyl]-1-methyl-1H-benzimidazole-5-yl]carbonyl]-N-2-pyridinyl-ethyl ester, methane sulfonate represented by Formula (I) below:

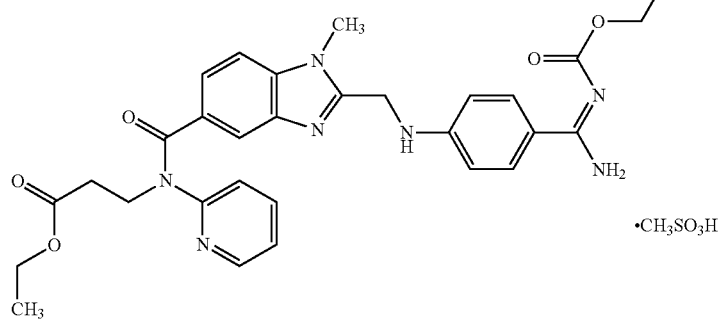
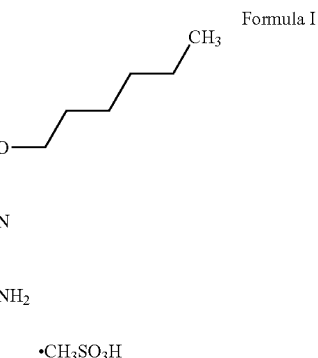

Formula I

·CH$_3$SO$_3$H

Dabigatran etexilate mesylate is commercially marketed as PRADAXA® by Boehringer Ingelheim Pharmaceuticals Inc. PRADAXA® is available as 75 mg capsule containing 86.48 mg dabigatran etexilate mesylate equivalent to 75 mg dabigatran etexilate and 150 mg capsule containing 172.95 mg dabigatran etexilate mesylate equivalent to 150 mg dabigatran etexilate. The recommended dose of PRADAXA® is one capsule taken twice a day with or without food. PRADAXA® is indicated to reduce the risk of stroke and systemic embolism in patients with non-valvular atrial fibrillation.

Dabigatran and its acyl glucuronides are competitive direct thrombin inhibitors. Because thrombin enables the conversion of fibrinogen into fibrin during the coagulation cascade, its inhibition prevents the development of a thrombus. Both free and clot-bound thrombin and thrombin-induced platelet aggregation are inhibited by active moieties.

WO9837075 discloses the preparation of substituted (4-benzimidazol-2yl-methylamino)-benzamidines, particularly Dabigatran etexilate. The process disclosed involves the use of column chromatography for purification thereby making the process ineffective at industrial scale. Further, 1-methyl-2-[N-[4-amidinophenyl]aminomethyl]benzimidazol-5-yl-carboxylic acid-N-(2-pyridyl)-N-(2-ethoxy carbonylethyl)amide mesylate compound is obtained in low yield.

WO2011061080 describes the preparation of Dabigatran etexilate by reacting Ethyl-3-{[(2-halomethyl-1-methyl-1H-benzimidazole-5-yl)carbonyl]-(2-pyridinyl)amino}propanoate with 4-aminobenzamidine-N-hexyl-carbamate.

CN102850326 discloses the process for preparation of Dabigatran etexilate by reacting O-mesyl derivative of Ethyl-3-{[(2-hydroxymethyl-1-methyl-1H-benzimidazole-5-yl)carbonyl]-(2-pyridinyl)amino}propanoate with 4-amino benzamidine-N-hexyl-carbamate.

WO2012153158 describes a process for preparation of Dabigatran etexilate or pharmaceutically acceptable salts thereof by using N-[4-(5-substituted-1,2,4-oxadiazol-3-yl)-phenyl]glycine. It further relates to various salts of Ethyl-N-[(2-{[4-carbamimidoylphenyl)amino]methyl}-1-methyl-1H-benzimidazole-5-yl)-carbonyl]-N-pyridine-2-yl/-β-alaninate.

There exists a need to develop a simple, cost-effective and commercially viable process for the preparation of Dabigatran etexilate or its pharmaceutically acceptable salts. The present invention provides an industrially viable process for preparation of Dabigatran etexilate or pharmaceutically acceptable salt thereof using novel compounds such as Ethyl-3-{[(2-formyl-1-methyl-1H-benzimidazole-5-yl)carbonyl]-(2-pyridinyl)amino}propanoate, Ethyl-3-{[(2-dihalomethyl-1-methyl-1H-benzimidazole-5-yl)carbonyl]-(2-pyridinyl)amino}propanoate, Ethyl-3-{[(1,2-dimethyl-1H-benzimidazole-5-yl)carbonyl]-(2-pyridinyl)amino}propanoate, or [(4-[{(hexyloxy)carbonyl]carbamimidoyl}phenyl)amino]acetic acid.

3

OBJECT OF THE INVENTION

An object of the present invention is to provide simple, cost effective and industrially viable process for preparation of Dabigatran etexilate or pharmaceutically acceptable salt thereof.

Another object of the present invention provides a novel compound selected from the group consisting of, Ethyl-3-{[(2-formyl-1-methyl-1H-benzimidazole-5-yl)carbonyl]-(2-pyridinyl)amino}propanoate, Ethyl-3-{[2-dihalomethyl-1-methyl-1H-benzimidazole-5-yl)carbonyl]-(2-pyridinyl) amino}propanoate, Ethyl-3-{[(1,2-dimethyl-1H-benzimidazole-5-yl)carbonyl]-(2-pyridinyl) amino}propanoate, or [(4-{[(hexyloxy)carbonyl] carbamimidoyl}phenyl)amino]acetic acid and process for preparation thereof.

Another object of the present invention provides a process for preparation of Dabigatran etexilate or pharmaceutically acceptable salt thereof using these novel compounds.

Another object of the present invention is to provide a process for preparation of Dabigatran etexilate mesylate from Dabigatran etexilate tetrahydrate.

SUMMARY OF THE INVENTION

An aspect of the present invention is to provide a process for preparation of Dabigatran etexilate or pharmaceutically acceptable salt thereof, comprising the steps of,
 a) treating Ethyl-3-{[(2-formyl-1-methyl-1H-benzimidazole-5-yl)carbonyl]-(2-pyridinyl)amino}propanoate with 4-aminobenzamidine or N-hydroxy-4-aminobenzamidine to obtain 1-methyl-2[N-[4-amidinophenyl] aminomethyl]-benzimidazol-5-yl-carboxylic acid-N-(2-pyridyl)-N-(2-ethoxycarbonyl ethyl)amide;
 b) optionally purifying said 1-methyl-2[N-[4-amidinophenyl]aminomethyl]-benzimidazol-5-yl-carboxylic acid-N-(2-pyridyl)-N-(2-ethoxy carbonyl ethyl)amide;
 c) converting said 1-methyl-2-[N-[4-amidinophenyl] aminomethyl]benzimidazol-5-yl-carboxylic acid-N-(2-pyridyl)-N-(2-ethoxycarbonyl ethyl)amide to Dabigatran etexilate or pharmaceutically acceptable salt thereof.

Preferably, said treatment in step a) is carried out in the presence of a reducing agent at a temperature of about 10° C. to 20° C. Preferably, said reaction is carried out in the presence of reducing agent selected from sodium borohydride, sodium cyanoborohydride, sodium triacetoxy borohydride, lithium borohydride, lithium aluminium hydride or diisobutylaluminium hydride; and solvent selected from acetic acid, formic acid, ethanol, methanol, isopropanol, n-propanol, n-butanol or mixture thereof and wherein said purification of 1-methyl-2-[N-[4-amidinophenyl]amino methyl]-benzimidazol-5-yl-carboxylic acid-N-(2-pyridyl)-N-(2-ethoxy carbonyl ethyl)amide is carried out by conversion to its acid addition salt.

Another aspect of the present invention is to provide a process for preparation of Dabigatran etexilate or pharmaceutically acceptable salt thereof, comprising the steps of,
 a) treating Ethyl-3-[(3-amino-4-methylaminobenzoyl)-N-(pyridin-2-yl)-amino]propanoate with acetic acid derivative to obtain Ethyl-3-{[(2-formyl-1-methyl-1H-benzimidazole-5-yl)carbonyl]-(2-pyridinyl) amino}propanoate;
 b) reacting Ethyl-3-{[(2-formyl-1-methyl-1H-benzimidazole-5-yl)carbonyl]-(2-pyridinyl)amino}propanoate with 4-aminobenzamidine or N-hydroxy-4-aminobenzamidine to obtain 1-methyl-2-[N-[4-amidinophenyl] amino methyl]-benzimidazol-5-yl-carboxylic acid-N-(2-pyridyl)-N-(2-ethoxy carbonyl ethyl)amide; and
 c) converting 1-methyl-2-[N-[4-amidinophenyl]amino methyl]-benzimidazol-5-yl-carboxylic acid-N-(2-pyridyl)-N-(2-ethoxy carbonyl ethyl)amide to Dabigatran etexilate or pharmaceutically acceptable salt thereof.

Preferably said acetic acid derivative is selected from dihaloacetyl halide, dihaloacetic acid, dihaloacetic anhydride, glycolic acid, acetyl halide, acetic acid, acetic anhydride or glyoxylic acid.

Another aspect of the present invention is to provide a process for preparation of Ethyl-3-{[(2-formyl-1-methyl-1H-benzimidazole-5-yl)carbonyl]-(2-pyridinyl) amino}propanoate, wherein said process comprises the steps of,
 a) treating Ethyl-3-[(3-amino-4-methylaminobenzoyl)-N-(pyridin-2-yl)-amino]propanoate with dichloroacetyl chloride, dichloroacetic anhydride or dichloroacetic acid to obtain Ethyl-3-{[(2-dichloromethyl-1-methyl-1H-benzimidazole-5-yl)carbonyl]-(2-pyridinyl) amino}propanoate;
 b) converting Ethyl-3-{[(2-dichloromethyl-1-methyl-1H-benzimidazole-5-yl)carbonyl]-(2-pyridinyl) amino}propanoate to Ethyl-3-{[(2-formyl-1-methyl-1H-benzimidazole-5-yl)carbonyl]-(2-pyridinyl) amino}propanoate, either by
  i. treating Ethyl-3-{[(2-dichloromethyl-1-methyl-1H-benzimidazole-5-yl)carbonyl]-(2-pyridinyl) amino}propanoate with an acetate forming agent in the presence of phase transfer catalyst to form the diacetate compound;
  ii. treating the diacetate compound with a base at a temperature of at least about 35° C. to obtain Ethyl-3-{[(2-dichloromethyl-1-methyl-1H-benzimidazole-5-yl)carbonyl]-(2-pyridinyl)amino}propanoate
  OR
  i. reacting Ethyl-3-{[(2-dichloromethyl-1-methyl-1H-benzimidazole-5-yl)carbonyl]-(2-pyridinyl) amino}propanoate with DMSO-base or sodium metaperiodate-DMF to obtain Ethyl-3-{[(2-formyl-1-methyl-1H-benzimidazole-5-yl)carbonyl]-(2-pyridinyl)amino}propanoate;
  ii. isolating Ethyl-3-{[(2-formyl-1-methyl-1H-benzimidazole-5-yl)carbonyl]-(2-pyridinyl) amino}propanoate.

Preferably said treatment in step a) is carried out at a temperature of about 40° C.-80° C. in the presence of solvent selected from THF, chlorobenzene, ethyl acetate, methyl acetate or butyl acetate. Preferably, said acetate forming agent is sodium acetate or potassium acetate and said phase transfer catalyst is a quaternary ammonium salt.

Another aspect of the present invention is to provide a process for preparation of Ethyl-3-{[(2-formyl-1-methyl-1H-benzimidazole-5-yl)carbonyl]-(2-pyridinyl) amino}propanoate, wherein said process comprises the steps of
 a) treating Ethyl-3-[(3-amino-4-methylaminobenzoyl)-N-(pyridin-2-yl)-amino]propanoate with glycolic acid in presence of solvent selected from toluene, xylene, heptane, cyclohexane, dichloromethane, dichloroethane or methyl tert butyl ether at reflux temperature to obtain Ethyl-3-{[(2-hydroxymethyl-1-methyl-1H-benzimidazole-5-yl)carbonyl]-(2-pyridinyl) amino}propanoate;
 b) treating Ethyl-3-{[(2-hydroxymethyl-1-methyl-1H-benzimidazole-5-yl)carbonyl]-(2-pyridinyl) amino}propanoate with oxidizing agent to Ethyl-3-{[(2-formyl-1-methyl-1H-benzimidazole-5-yl) carbonyl]-(2-pyridinyl)amino}propanoate.

Another aspect of the present invention is to provide a process for preparation of Ethyl-3-{[(2-formyl-1-methyl- 1H-benzimidazole-5-yl)carbonyl]-(2-pyridinyl)amino}propanoate, wherein said process comprises the steps of
  a) treating Ethyl-3-[(3-amino-4-methylaminobenzoyl)-N-(pyridin-2-yl)-amino]propanoate with acetic acid, acetic anhydride, acetyl chloride or acetyl bromide to obtain Ethyl-3-{[1,2-dimethyl-1H-benzimidazol-5-yl)carbonyl]-(2-pyridinyl)amino}propanoate;
  b) optionally, treating Ethyl-3-{[1,2-dimethyl-1H-benzimidazol-5-yl)carbonyl]-(2-pyridinyl)amino}propanoate with a halogenating agent to obtain Ethyl-3-{[(2-dihalomethyl-1-methyl-1H-benzimidazole-5-yl)carbonyl]-(2-pyridinyl)amino}propanoate;
  c) treating said Ethyl-3-{[1,2-dimethyl-1H-benzimidazol-5-yl)carbonyl]-(2-pyridinyl)amino}propanoate or said Ethyl-3-{[(2-dihalomethyl-1-methyl-1H-benzimidazole-5-yl)carbonyl]-(2-pyridinyl)amino}propanoate with oxidizing agent to Ethyl-3-{[(2-formyl-1-methyl-1H-benzimidazole-5-yl)carbonyl]-(2-pyridinyl)amino}propanoate.

Preferably, said oxidizing agent is selected from selenium dioxide, chromyl chloride, chromium trioxide, potassium permaganate, manganese dioxide, ceric ammonium nitrate, ceric trifluoroacetate, pyridinium chlorochromate, silver oxide or Bromine-DMSO and said halogenating agent is selected from N-halosuccinimide, chlorine, bromine, hypochlorite or hypobromite.

Another aspect of the present invention is to provide a process for preparation of Ethyl-3-{[(2-formyl-1-methyl-1H-benzimidazole-5-yl)carbonyl]-(2-pyridinyl)amino}propanoate, wherein said process comprises treating Ethyl-3-[(3-amino-4-methyl aminobenzoyl)-N-(pyridin-2-yl)-amino]propanoate with glyoxylic acid to obtain Ethyl-3-{[(2-formyl-1-methyl-1H-benzimidazole-5-yl)carbonyl]-(2-pyridinyl)amino}propanoate Another aspect of the present invention is to provide a process for preparation of Dabigatran etexilate or pharmaceutically acceptable salt thereof, comprising the steps of,
  a) purification of 1-methyl-2-[N-[4-amidinophenyl]aminomethyl]-benzimidazol-5-yl-carboxylic acid-N-(2-pyridyl)-N-(2-ethoxy carbonylethyl)amide by conversion to its acid addition salt, preferably mesylate or tosylate; and
  b) treating said 1-methyl-2-[N-[4-amidinophenyl]aminomethyl]benzimidazol-5-yl-carboxylic acid-N-(2-pyridyl)-N-(2-ethoxycarbonyl ethyl)amide or salt thereof with n-hexyl chloroformate to obtain Dabigatran etexilate or pharmaceutically acceptable salt.

Another aspect of the present invention is to provide a compound of formula II

Formula II

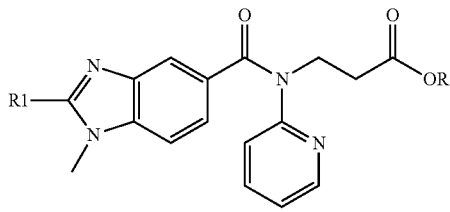

wherein R=H or $C_1$-$C_5$ alkyl; and $R_1$=—CHO or —$CH_3$, or —$CHX_2$, where X=—Cl, —Br, —I
Preferably, when R1=—CHO, R=—H, —$CH_3$ or —$C_2H_5$;
when R1=—$CHCl_2$, R=—H, —$CH_3$ or —$C_2H_5$;
when R1=—$CH_3$, R=—H, —$CH_3$ or —$C_2H_5$.

Preferably, the compound of Formula II is selected from the group consisting of,
Ethyl-3-{[(2-dichloromethyl-1-methyl-1H-benzimidazole-5-yl)carbonyl]-(2-pyridinyl)amino}propanoate;
Ethyl-3-{[(2-formyl-1-methyl-1H-benzimidazole-5-yl)carbonyl]-(2-pyridinyl)amino}propanoate;
3-{[(2-dichloromethyl-1-methyl-1H-benzimidazole-5-yl)carbonyl]-(2-pyridinyl)amino}propanoic acid; and
3-{[(2-formyl-1-methyl-1H-benzimidazole-5-yl)carbonyl]-(2-pyridinyl)amino}propanoic acid.

Preferably, the compound of Formula II is selected from the group consisting of,
Methyl-3-{[(2-dichloromethyl-1-methyl-1H-benzimidazole-5-yl)carbonyl]-(2-pyridinyl)amino}propanoate;
Methyl-3-{[(2-formyl-1-methyl-1H-benzimidazole-5-yl)carbonyl]-(2-pyridinyl)amino}propanoate;
Ethyl-3-{[(1,2-dimethyl-1H-benzimidazol-5-yl)carbonyl]-(2-pyridinyl)amino}propanoate;
Methyl-3-{[(1,2-dimethyl-1H-benzimidazol-5-yl)carbonyl]-(2-pyridinyl)amino}propanoate; and
3-{[(1,2-dimethyl-1H-benzimidazol-5-yl)carbonyl]-(2-pyridinyl)amino}propanoic acid.

Preferably the compounds of Formula II are used in the preparation of Dabigatran etexilate.

Another aspect of the present invention provides a process for preparation of compound of Formula II, where R1=—CHO, R=—H or —$C_2H_5$, wherein the process comprises reacting 2-formyl-1-methyl-1H-benzimidazole-5-carboxylic acid with 3-[N-(2-pyridinyl)-amino]propanoic acid or ethyl ester thereof in presence of a halogenating agent selected from thionyl chloride, phosphorus trichloride or phosphorus pentachloride to obtain 3-{[(2-formyl-1-methyl 1H-benzimidazole-5-yl)carbonyl]-(2-pyridinyl)amino}propanoic acid or ethyl ester thereof.

Another aspect of the present invention provides a process for preparation of 2-formyl-1-methyl-1H-benzimidazole-5-carboxylic acid comprising the steps of,
  a) treating 3-amino-4-(methylamino)benzoic acid or esters thereof with dihaloacetyl halide, dihaloacetic anhydride or dihaloacetic acid to obtain 2-(dihalomethyl)-1-methyl-1H-benzimidazole-5-carboxylic acid or ester thereof;
  b) treating 2-(dihalomethyl)-1-methyl-1H-benzimidazole-5-carboxylic acid or ester thereof with DMSO-base or sodium metaperiodate-DMF to obtain 2-formyl-1-methyl-1H-benzimidazole-5-carboxylic acid.
OR
  a) treating 3-amino-4-(methylamino)benzoic acid or esters thereof with glycolic acid to obtain 2-hydroxymethyl-1-methyl-1H-benzimidazole-5-carboxylic acid or ester thereof;
  b) subjecting 2-hydroxymethyl-1-methyl-1H-benzimidazole-5-carboxylic acid or ester thereof to oxidation using manganese dioxide, Dess-Martin periodinane or pyridinium chloroformate to obtain 2-formyl-1-methyl-1H-benzimidazole-5-carboxylic acid.
OR
  a) treating 3-amino-4-(methylamino)benzoic acid or esters thereof with acetic acid, acetic anhydride, acetyl chloride or acetyl bromide to obtain 1,2-dimethyl-1H-benzimidazole-5-carboxylic acid or ester thereof; and
  b) subjecting 1,2-dimethyl-1H-benzimidazole-5-carboxylic acid or ester thereof to oxidation using manganese dioxide, Dess-Martin periodinane or pyridinium chloroformate to obtain 2-formyl-1-methyl-1H-benzimidazole-5-carboxylic acid.

OR treating 3-amino-4-(methylamino) benzoic acid or ester thereof with glyoxylic acid to obtain 2-formyl-1-methyl-1H-benzimidazole-5-carboxylic acid or ester thereof.

Another aspect of the present invention provides a process for preparation of Dabigatran etexilate comprising the steps of, a) reacting (4-amidinophenyl)glycine alkyl ester with n-hexyl chloroformate followed by hydrolysis to obtain [(4-{[(hexyloxy)carbonyl]carbamimidoyl}phenyl)amino]acetic acid;

b) coupling Ethyl-3-[(3-amino-4-methylaminobenzoyl)-N-(pyridin-2-yl)-amino]propanoate with [(4-{[(hexyloxy)carbonyl]carbamimidoyl}phenyl)amino]acetic acid to obtain Dabigatran etexilate; and c) optionally converting Dabigatran etexilate to its pharmaceutically acceptable salt.

Preferably, 4-aminobenzonitrile is reacted with haloacetic acid alkyl ester to obtain N-(4-cyanophenyl)glycine alkyl ester; subjecting N-(4-cyanophenyl)glycine alkyl ester to Pinner reaction in presence of alcohol, acid and base to obtain (4-amidinophenyl)glycine alkyl ester;

Another aspect of the present invention provides a compound of formula VII,

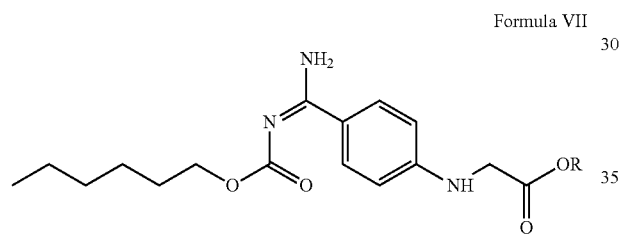

Formula VII where R=H or $C_1$-$C_3$alkyl

Another aspect of the present invention provides a process for conversion of Dabigatran etexilate to Dabigatran etexilate mesylate, by a process comprising, a) treating Dabigatran etexilate in a solvent selected from acetone, acetonitrile, tetrahydrofuran, ethyl acetate, methyl acetate, dimethyl formamide, dimethyl acetamide or dimethyl sulfoxide to obtain a solution;

b) treating the solution of step a) with methane sulfonic acid to obtain a mixture; and c) isolating Dabigatran etexilate mesylate Form I from said mixture.

Preferably, said Dabigatran etexilate is Dabigatran etexilate anhydrous Form I.

Another aspect of the present invention provides a process for conversion of Dabigatran etexilate tetrahydrate to Dabigatran etexilate mesylate, by a process comprising the steps of, a) obtaining a solution of Dabigatran etexilate tetrahydrate;

b) adding the obtained solution to a solution of methanesulfonic acid to obtain a mixture;

c) isolating Dabigatran etexilate mesylate Form I from said mixture.

DESCRIPTION OF THE INVENTION

Figure 1:
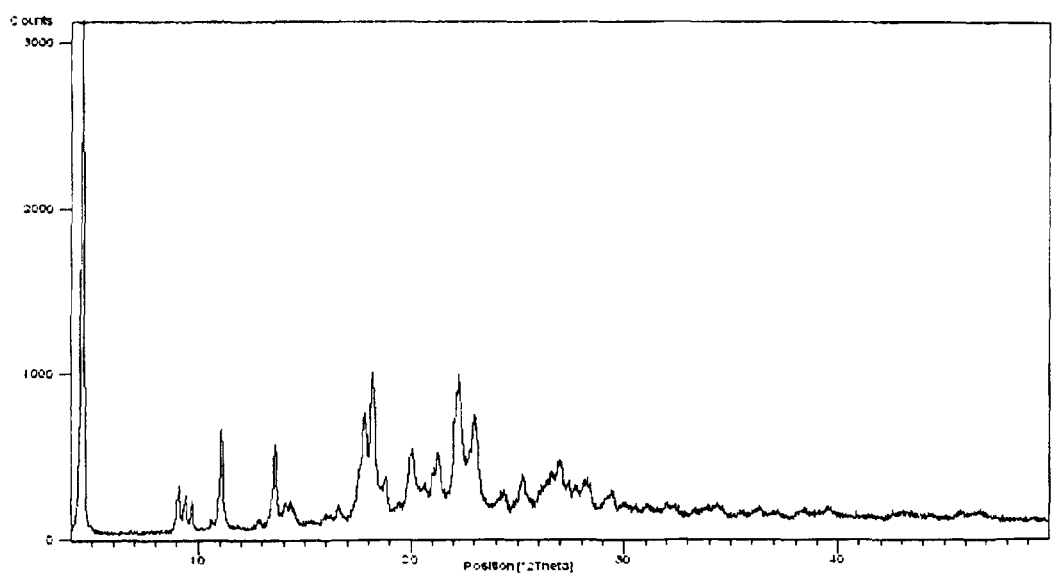
FIG. 1: X-ray powder diffraction pattern of Dabigatran etexilate mesylate Form I.

The present invention provides a process for preparation of Dabigatran etexilate or pharmaceutically acceptable salt thereof.

According to one embodiment of the present invention, there is provided a process for preparation of Dabigatran etexilate or pharmaceutically acceptable salt thereof which comprises the steps of, a) treating Ethyl-3-{[(2-formyl-1-methyl-1H-benzimidazole-5-yecarbonyl]-(2-pyridinyl)amino}propanoate (II) with 4-aminobenzamidine (III) or N-hydroxy-4-aminobenzamidine to obtain 1-methyl-2-[N-[4-amidinophenyl]aminomethyl]-benzimidazol-5-yl-carboxylic acid-N-(2-pyridyl)-N-(2-ethoxy carbonylethyl)amide (IV);

b) optionally purifying 1-methyl-2-[N-[4-amidinophenyl]aminomethyl]-benzimidazol-5-yl-carboxylic acid-N-(2-pyridyl)-N-(2-ethoxy carbonyl ethyl)amide (IV);

c) converting 1-methyl-2-[N-[4-amidinophenyl]aminomethyl]benzimidazol-5-yl-carboxylic acid-N-(2-pyridyl)-N-(2-ethoxycarbonylethyl)amide (IV) to Dabigatran etexilate (V) or pharmaceutically acceptable salt thereof.

Reaction of Ethyl-3-{[(2-formyl-1-methyl-1H-benzimidazole-5-yl)carbonyl]-(2-pyridinyl)amino}propanoate (II) with 4-aminobenzamidine (III) or N-hydroxy-4-aminobenzamidine is carried out in presence of a reducing agent selected from sodium borohydride, sodium cyanoborohydride, sodium triacetoxy borohydride, lithium borohydride, lithium aluminium hydride or diisobutylaluminium hydride, preferably sodium borohydride.

Scheme 1

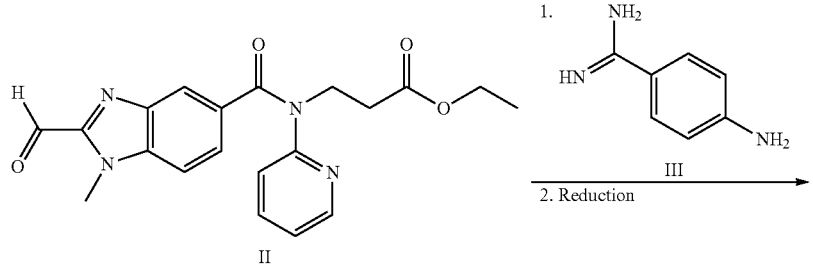

-continued

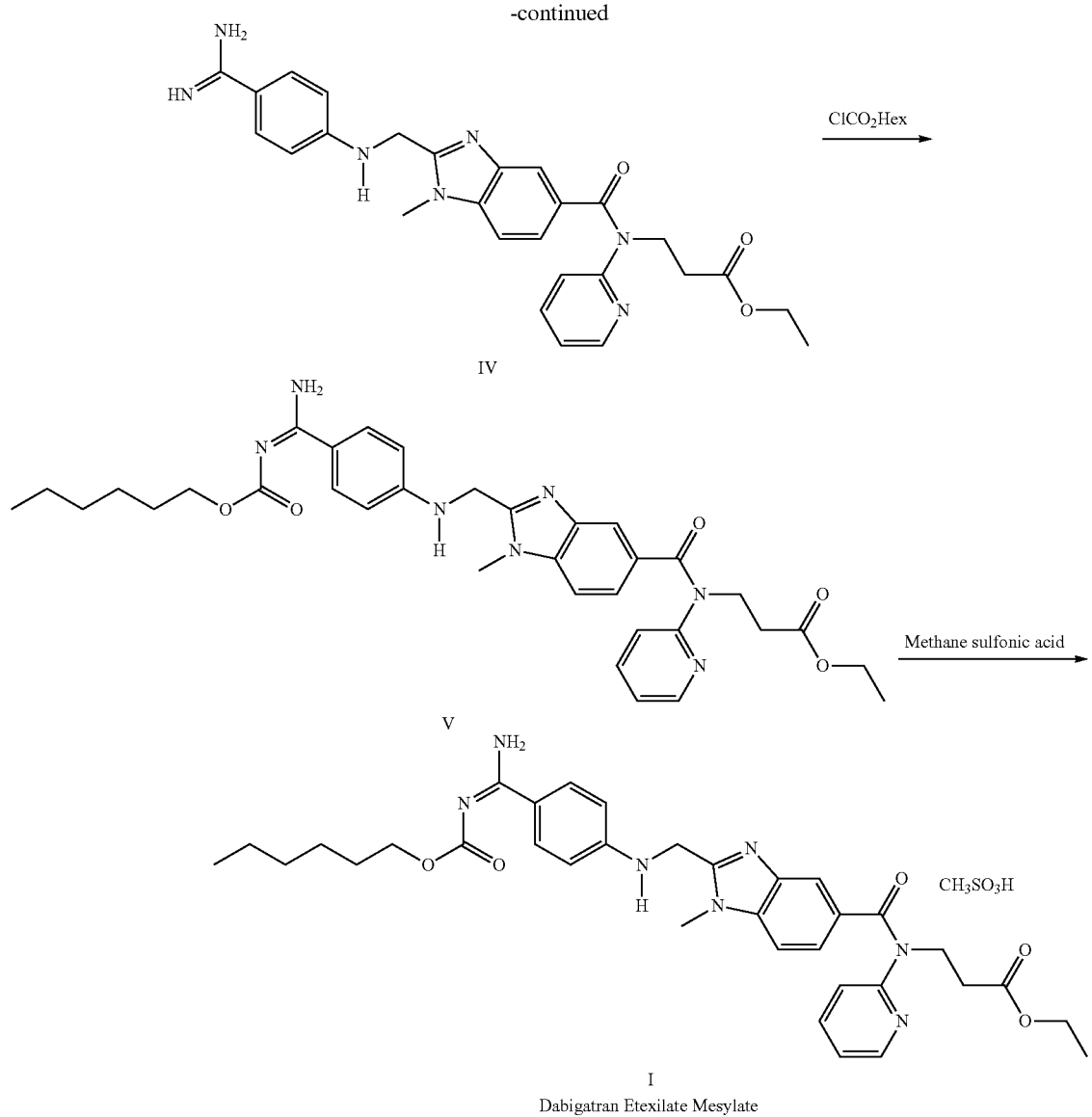

I
Dabigatran Etexilate Mesylate

According to a preferred embodiment of the present invention, there is provided a process for preparation of Dabigatran etexilate mesylate comprising, Step I: Ethyl-3-{[(2-formyl-1-methyl-1H-benzimidazole-5-yl)carbonyl]-(2-pyridinyl)amino}propanoate (II) is reacted with 4-aminobenzamidine (III) in presence of solvent selected from acetic acid, formic acid, ethanol, methanol, isopropanol, n-propanol or n-butanol, preferably acetic acid at 20 to 30° C., preferably 25 to 28° C. The reaction mixture is stirred for 1 to 3 hours, preferably for 2 hours and cooled to 10 to 20° C., preferably 5 to 20° C., more preferably 10 to 20° C., most preferably 14 to 18° C. To this mixture, is added sodium borohydride in a lot wise manner, preferably in five lots. The reaction mixture is stirred at the same temperature for 1 to 3 hours, preferably for 2 hours. The mixture is concentrated under vacuum to obtain a semisolid residue. This semisolid residue is dissolved in solvent selected from ethanol, methanol, propanol or butanol, preferably ethanol at 50 to 70° C., preferably at 55-60° C. The solution is further cooled to 20 to 30° C., preferably 25° C. followed by addition of methanesulfonic acid. The mixture is further diluted with a solvent selected from acetone, tetrahydrofuran (THF), acetonitrile, ethyl acetate, methyl acetate, dimethyl formamide, dimethylacetamide, dimethylsulfoxide (DMSO), methyl tert butyl ether (MTBE), diisopropyl ether (DIPE), 1,4-dioxane or methyl tetrahydrofuran, preferably acetone and stirred for 3 to 6 hours, preferably for 4 to 5 hours at the same temperature. The obtained slurry is filtered and the solid is washed with acetone and dried to obtain 1-methyl-2-[N-[4-amidinophenyl]aminomethyl]benzimidazol-5-yl-carboxylic acid-N-(2-pyridyl)-N-(2-ethoxy carbonyl ethyl)amide methane sulfonate salt.

Step II: The obtained 1-methyl-2-[N-[4-amidinophenyl]aminomethyl]benzimidazol-5-yl-carboxylic acid-N-(2-pyridyl)-N-(2-ethoxy carbonyl ethyl)amide methane sulfonate salt is converted to Dabigatran etexilate mesylate by the processes known in the prior art or by the process of the present invention. The process is represented in the above Scheme 1.

According to one embodiment of the present invention, there is provided a process for preparation of Ethyl-3-{[(2- formyl-1-methyl-1H-benzimidazole-5-yl)carbonyl]-(2-pyridinyl)amino}propanoate, intermediate used in the synthesis of Dabigatran etexilate, comprising treating Ethyl-3-[(3-amino-4-methylaminobenzoyl)-N-(pyridin-2-yl)-amino]propanoate (VI) with acetic acid derivative to obtain Ethyl-3-{[(2-formyl-1-methyl-1H-benzimidazole-5-yl)carbonyl]-(2-pyridinyl)amino}propanoate;

Acetic acid derivative is selected from dihaloacetyl halide, dihaloacetic acid, dihaloacetic anhydride, glycolic acid, acetic acid, acetic anhydride, acetyl halide or glyoxylic acid. The halide is selected from chloro, bromo or iodo, preferably, chloro.

In one embodiment of the present invention, there is provided a process for preparation of Ethyl-3-{[(2-formyl-1-methyl-1H-benzimidazole-5-yl)carbonyl]-(2-pyridinyl)amino}propanoate comprising the steps of, a) treating Ethyl-3-[(3-amino-4-methylaminobenzoyl)-N-(pyridin-2-yl)-amino]propanoate with dichloroacetyl chloride, dichloroacetic anhydride or dichloroacetic acid, preferably dichloroacetyl chloride to obtain Ethyl-3-{[(2-dichloromethyl-1-methyl-1H-benzimidazole-5-yl)carbonyl]-(2-pyridinyl)amino}propanoate;

b) converting Ethyl-3-{[(2-dichloromethyl-1-methyl-1H-benzimidazole-5-yl)carbonyl]-(2-pyridinyl)amino}propanoate to Ethyl-3-{[(2-formyl-1-methyl-1H-benzimidazole-5-yl)carbonyl]-(2-pyridinyl)amino}propanoate.

Addition of dichloroacetyl compound such as dichloroacetyl chloride, dichloroacetic anhydride or dichloroacetic acid is carried out at low temperature so as to prevent its initial decomposition.

Conversion of Ethyl-3-{[(2-dichloro methyl-1-methyl-1H-benzimidazole-5-yl)carbonyl]-(2-pyridinyl)amino}propanoate to Ethyl-3-{[(2-formyl-1-methyl-1H-benzimidazole-5-yl)carbonyl]-(2-pyridinyl)amino}propanoate comprises treating Ethyl-3-{[(2-dichloromethyl-1-methyl-1H-benzimidazole-5-yl)carbonyl]-(2-pyridinyl)amino}propanoate with an acetate forming agent in presence of phase transfer catalyst to form the diacetate compound; treating the obtained diacetate compound with a base at a temperature of at least about 35° C. to obtain Ethyl-3-{[(2-formyl-1-methyl-1H-benzimidazole-5-yl)carbonyl]-(2-pyridinyl)amino}propanoate.

Any phase transfer catalyst known in the art can be used. Preferably quaternary ammonium salts such as tetrabutylammonium bromide, tetrabutylammonium chloride, tetrabutylammonium iodide, tetrabutylammonium hydroxide, tetraethylammonium chloride, tetramethylammonium bromide, trioctylmethylammonium chloride, trioctylpropylammonium chloride or tetrapropylammonium bromide can be used. Other ester forming agents can be used in place of acetate forming agent, for example formate forming agents.

Alternatively, Ethyl-3-{[(2-dichloromethyl-1-methyl-1H-benzimidazole-5-yl)carbonyl]-(2-pyridinyl)amino}propanoate is treated with DMSO-base or sodium metaperiodate (NaIO4)-DMF to obtain Ethyl-3-{[(2-formyl-1-methyl-1H-benzimidazole-5-yl)carbonyl]-(2-pyridinyl)amino}propanoate.

In a preferred embodiment, Ethyl-3-[(3-amino-4-methylaminobenzoyl)-N-(pyridin-2-yl)-amino]propanoate is treated with solvent selected from acetonitrile, THF, ethyl acetate or chlorobenzene to obtain a mixture. This mixture is cooled to about −20 to −10° C., preferably −15° C. To this chilled suspension, a solution of dichloroacetyl chloride in solvent selected from acetonitrile, THF, ethyl acetate or chlorobenzene is added at the same temperature over period of 2 hours. The reaction mass is maintained at the same temperature for 1 hour. The reaction mass is heated to a temperature of 50 to 60° C. The reaction mass is maintained at this temperature till reaction completion is achieved. The reaction mass is quenched and then filtered. The cake obtained is washed with water and dried. The solid thus obtained is treated with a solvent selected from isopropanol, methanol, ethanol or MTBE to obtain Ethyl-3-{[(2-dichloromethyl-1-methyl-1H-benzimidazole-5-yl)carbonyl]-(2-pyridinyl)amino}propanoate.

Ethyl-3-{[(2-dichloro methyl-1-methyl-1H-benzimidazole-5-yl)carbonyl]-(2-pyridinyl)amino}propanoate thus obtained is treated with a solvent selected from toluene, DMSO or DMF to obtain a mixture. To this mixture, is added acetate forming agent such as sodium acetate or potassium acetate and tetrabutyl ammonium bromide as phase transfer catalyst. The reaction mixture is heated to about 85 to 95° C., preferably 90° C. The reaction mixture is maintained at the same temperature for about 2 to 5 hours, preferably, 3 to 4 hours. After the completion of the reaction, the mixture is filtered and the filtrate is concentrated to get a light brown coloured oil. This oil is treated with a base selected from sodium carbonate, potassium carbonate, NaOH, KOH or the like, preferably in presence of tetrabutyl ammonium bromide. This mixture is then heated at about 40° C. to 60° C., preferably 40° C. The reaction mixture is maintained under stirring at the same temperature for 1 hour. The reaction mixture is further maintained under stirring at ambient temperature for about 4 to 6 hours. The solid thus obtained is filtered, washed and dried. The product thus obtained has a purity of about 95%.

In another preferred embodiment, Ethyl-3-[(3-amino-4-methylaminobenzoyl)-N-(pyridin-2-yl)-amino]propanoate (VI) is suspended in solvent selected from ethyl acetate, methyl acetate, butyl acetate or THF, preferably ethyl acetate at 10 to 30° C., preferably at 20° C. Dichloroacetic acid anhydride is added to the suspension followed by heating the suspension to a temperature of about 60 to 70° C. After a period of 1 to 3 hours, a base selected from potassium carbonate, sodium carbonate, lithium carbonate, cesium carbonate, sodium bicarbonate, potassium bicarbonate, triethyl amine (TEA) or N-methyl morpholine is added to the suspension at a temperature of about 30 to 50° C. This mixture is stirred for a further period of about 1 hour. The mixture is filtered and the filtrate is washed with solvent selected from ethyl acetate, methyl acetate, butyl acetate or THF, preferably ethyl acetate. The filtrate is evaporated under vacuum to reduce the volume and further treated with solvent selected from dimethyl sulfoxide, dimethyl formamide, dimethyl acetamide, acetonitrile, acetone, tetrahydrofuran, ethyl acetate, methyl acetate or mixture thereof. The obtained mixture is cooled and filtered. The product obtained is washed with solvent selected from dimethyl sulfoxide, dimethyl formamide, dimethyl acetamide, acetonitrile, acetone, tetrahydrofuran, ethyl acetate, methyl acetate or mixture thereof and dried to obtain Ethyl-3-{[(2-dichloromethyl-1-methyl-1H-benzimidazole-5-yl)carbonyl]-(2-pyridinyl)amino}propanoate.

The obtained Ethyl-3-{[(2-dichloromethyl-1-methyl-1H-benzimidazole-5-yl)carbonyl]-(2-pyridinyl)amino}propanoate is subjected to oxidation using DMSO-base, sodium metaperiodate (NaIO4)-DMF or the like to obtain Ethyl-3-{[(2-formyl-1-methyl-1H-benzimidazole-5-yl)carbonyl]-(2-pyridinyl)amino}propanoate.

This process is represented in Scheme 2 below,

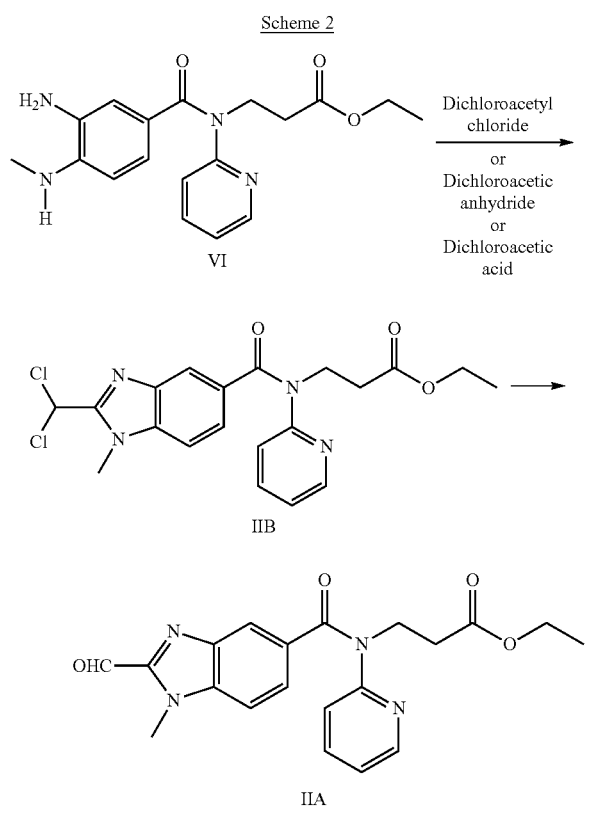

In a preferred embodiment, Ethyl-3-[(3-amino-4-methylamino benzoyl)-N-(pyridin-2-yl)-amino]propanoate and glycolic acid are refluxed in presence of solvent selected from toluene, xylene, heptane, cyclohexane, dichloroethane, dichloromethane or methyl tert-butyl ether, preferably toluene. The reaction mixture is stirred at the same temperature for 18 to 25 hours, preferably for 20 to 22 hours. After completion of reaction, the mixture is cooled to 40 to 60° C., preferably 50 to 55° C. followed by concentration under vacuum to obtain an oil. The oil is dissolved in a solvent selected from dichloromethane, dichloroethane, chloroform or carbon tetrachloride, preferably dichloromethane. The organic layer is extracted with saturated sodium bicarbonate solution followed by water. The organic layer is separated and concentrated to obtain a residue. The residue is treated with solvent selected from hexane, heptane, pentane, cyclopentane, cyclohexane, toluene or xylene, preferably hexane to obtained a slurry. The obtained slurry is stirred for about ½ hour to 1 hour at ambient temperature. The slurry is filtered and the solid obtained is washed with hexane. The wet cake obtained is dissolved in a solvent selected from acetonitrile, acetone, tetrahydrofuran (THF), ethyl acetate, methyl acetate, dimethyl formamide, dimethylacetamide or dimethyl sulfoxide (DMSO), preferably acetonitrile at 40 to 60° C., preferably at 45 to 50° C. to obtain a solution. The solution is cooled and maintained under stirring to obtain a slurry. The slurry is filtered and the obtained solid is washed and dried to obtain Ethyl-3-{[(2-hydroxymethyl-1-methyl-1H-benzimidazole-5-yl)carbonyl]-(2-pyridinyl)amino}propanoate.

Ethyl-3-{[(2-hydroxymethyl-1-methyl-1H-benzimidazole-5-yl)carbonyl]-(2-pyridinyl)amino}propanoate is treated with an oxidizing agent selected from manganese dioxide, Dess-Martin periodinane or pyridinium chloroformate, preferably manganese dioxide in presence of solvent selected from dichloromethane, dichloroethane, chloroform, carbon tetrachloride, THF, methyl-THF, 1,4-dioxane or toluene, preferably dichloromethane to obtain a mixture. The resultant mixture is stirred at 25 to 30° C. for 20 to 30 hours, preferably for 24 hours. The reaction mixture is filtered and the obtained solid is washed with solvent selected from dichloromethane, dichloroethane, chloroform or carbon tetrachloride, preferably dichloromethane. The filtrate is concentrated under vacuum to obtain a solid. The obtained solid is treated with solvent selected from hexane, heptane, pentane or toluene and the obtained slurry is filtered to obtain Ethyl-3-{[(2-formyl-1-methyl-1H-benzimidazole-5-yl)carbonyl]-(2-pyridinyl)amino}propanoate.

The process is represented in Scheme 3 below,

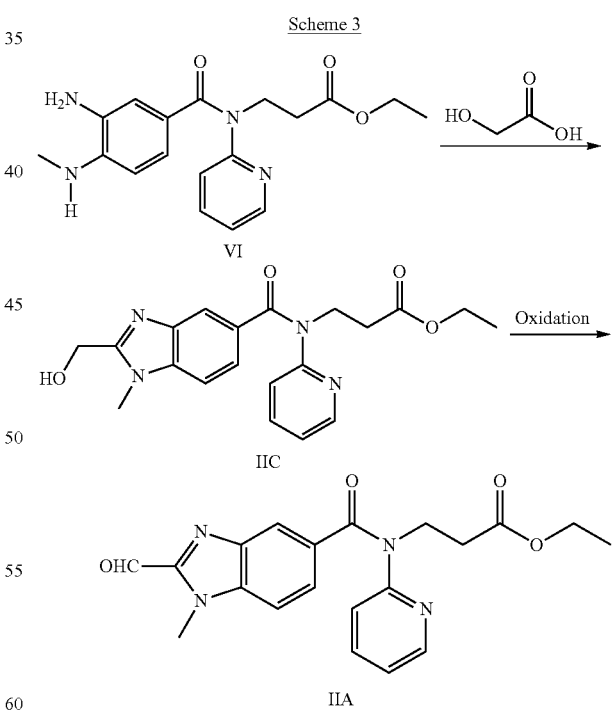

According to another embodiment of the present invention, there is provided a process for preparation of Ethyl-3-{[(2-formyl-1-methyl-1H-benzimidazol-5-yl) carbonyl]-(2-pyridinyl)amino}propanoate, an intermediate used in the synthesis of Dabigatran, which comprises the steps of, a) treating Ethyl-3-[(3-amino-4-methylaminobenzoyl)-N-(pyridin-2-yl)-amino]propanoate with acetic acid, acetic anhydride, acetyl chloride or acetyl bromide to obtain Ethyl-3-{[(1,2-dimethyl-1H-benzimidazol-5-yl)carbonyl]-(2-pyridinyl)amino}propanoate; and
b) optionally, treating Ethyl-3-{[(1,2-dimethyl-1H-benzimidazol-5-yl)carbonyl]-(2-pyridinyl)amino}propanoate with a halogenating agent to obtain Ethyl-3-{[2-dihalomethyl-1-methyl-1H-benzimidazol-5-yl)carbonyl]-(2-pyridinyl) amino}propanoate;
c) converting the obtained Ethyl-3-{[(1,2-dimethyl-1H-benzimidazol-5-yl)carbonyl]-(2-pyridinyl)amino}propanoate or Ethyl-3-{[2-dihalomethyl-1-methyl-1H-benzimidazol-5-yl)carbonyl]-(2-pyridinyl)amino}propanoate to Ethyl-3-{[(2-formyl-1-methyl-1H-benzimidazole-5-yl)carbonyl]-(2-pyridinyl)amino}propanoate.

Oxidizing agent is selected from selenium dioxide, chromyl chloride, chromium trioxide, potassium permaganate, manganese dioxide, ceric ammonium nitrate, ceric trifluoroacetate, pyridinium chlorochromate, silver oxide or Bromine-DMSO, preferably selenium dioxide.

In a preferred embodiment of the present invention, Ethyl-3-[(3-amino-4-methylaminobenzoyl)-N-(pyridin-2-yl)-amino]propanoate is treated with acetic acid to obtain a mixture. The resultant mixture is heated to reflux and maintained under stirring at the same temperature for about 4 to 8 hours, preferably for 5 to 6 hours. After completion of reaction, the mixture is cooled to 40 to 60° C., preferably 50 to 55° C. and then concentrated to obtain a semisolid. The semisolid is treated with water to obtain a mixture. This mixture is cooled to about 10 to 20° C. The pH of the mixture is adjusted to 7 using a base such as sodium bicarbonate and the mixture is stirred for about ½ hour to 1 hour. The mixture is filtered and the obtained solid is washed and dried to obtain Ethyl-3-{[(1,2-dimethyl-1H-benzimidazol-5-yl)carbonyl]-(2-pyridinyl)amino}propanoate.

The obtained Ethyl-3-{[(1,2-dimethyl-1H-benzimidazole-5-yl)carbonyl]-(2-pyridinyl)amino}propanoate is treated with selenium dioxide in the presence of a solvent selected from 1,4-dioxane, tetrahydrofuran (THF), diisopropyl ether, methyl tertiary butyl ether, dichloromethane, dichloroethane, chloroform, carbon tetrachloride or methyl THF, preferably 1,4-dioxane at ambient temperature to obtain a mixture. This mixture is heated to a temperature of about 70 to 90° C., preferably 80 to 85° C. for a period of 4 to 8 hours, preferably for 5 to 6 hours. The mixture is cooled and filtered. The filtrate is concentrated under vacuum to obtain an oily mass. The oily mass is diluted with a solvent selected from ethyl acetate, methyl acetate, butyl acetate, dichloromethane, dichloroethane, chloroform or carbon tetrachloride, preferably ethyl acetate to obtain a mixture. This mixture is filtered through hyflo bed and the filtrate is concentrated to obtain a residue. The obtained residue is treated with solvent selected from hexane, heptane, pentane or toluene. The obtained slurry is filtered to obtain Ethyl-3-{[(2-formyl-1-methyl-1H-benzimidazole-5-yl)carbonyl]-(2-pyridinyl) amino}propanoate.

In an alternate embodiment, Ethyl-3-{[(1,2-dimethyl-1H-benzimidazole-5-yl)carbonyl]-(2-pyridinyl)amino}propanoate is reacted with N-halosuccinimide such as N-chlorosuccinimide or N-bromosuccinimide in presence of initiator such as Azobisisobutyronitrile or benzoyl peroxide at ambient temperature in solvent selected from dichloromethane, dichloroethane, chloroform, carbon tetrachloride or the like, to obtain Ethyl-3-{[(2-dihalomethyl-1-methyl-1H-benzimidazole-5-yl)carbonyl]-(2-pyridinyl)amino}propanoate.

The obtained Ethyl-3-{[(2-dihalomethyl-1-methyl-1H-benzimidazole-5-yl)carbonyl]-(2-pyridinyl)amino}propanoate is treated with reagent selected from DMSO-base, hexamethylenetetramine, sodium metaperiodate-DMF, sodium acetate, sodium perchlorate, aqueous p-toluenesulfonic acid, sulfuric acid or the like to obtain Ethyl-3-{[(2-formyl-1-methyl-1H-benzimidazole-5-yl)carbonyl]-(2-pyridinyl)amino}propanoate.

The process is represented in Scheme 4 below,

Scheme 4

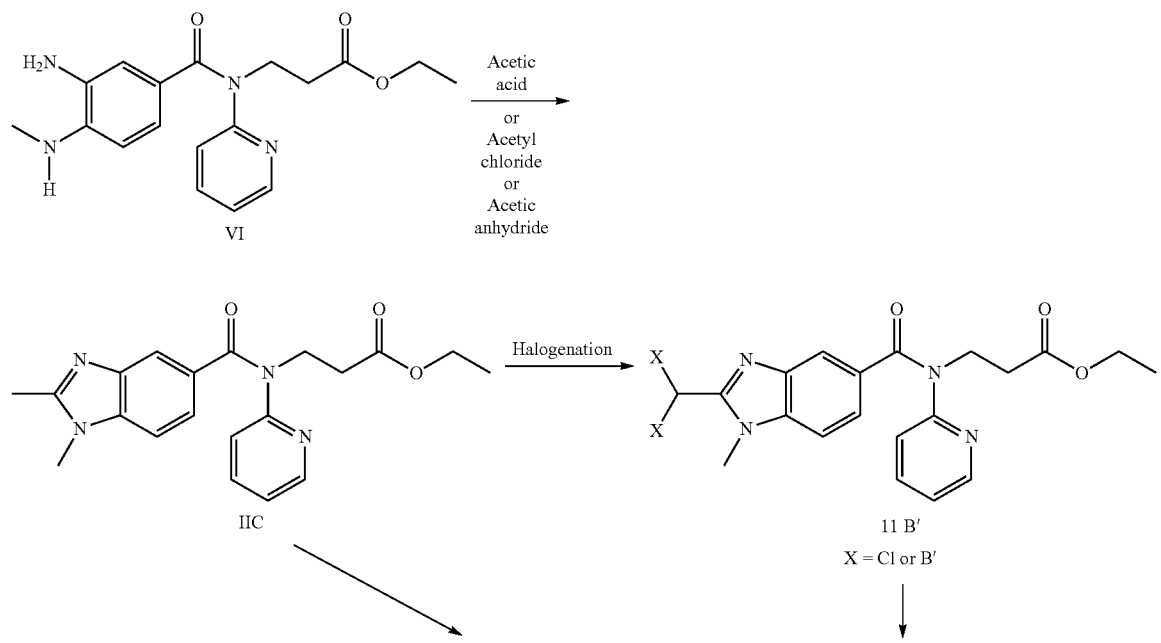

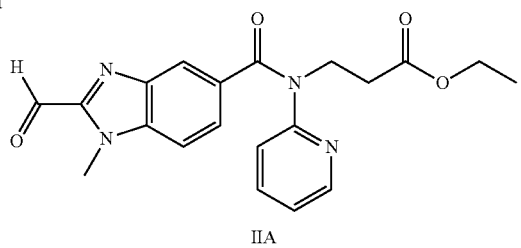

IIA

Yet another embodiment provides a process for preparation of Ethyl-3-{[(2-formyl-1-methyl-1H-benzimidazole-5-yl)carbonyl]-(2-pyridinyl)amino}propanoate which involves reacting Ethyl-3-[(3-amino-4-methylaminobenzoyl)-N-(pyridin-2-yl)-amino]propanoate with glyoxylic acid in presence of solvent selected from toluene, xylene, heptane or cyclohexane at reflux temperature to obtain Ethyl-3-{[(2-formyl-1-methyl-1H-benzimidazole-5-yl)carbonyl]-(2-pyridinyl)amino}propanoate.

The process is represented in Scheme 5 below,

Scheme 5

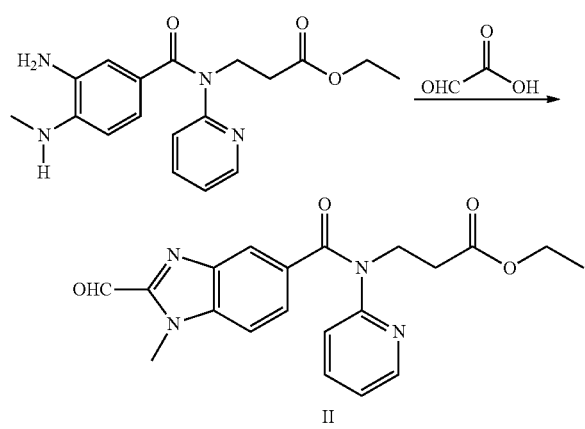

II

Another embodiment of the present invention provides a novel compound of formula II, Formula II

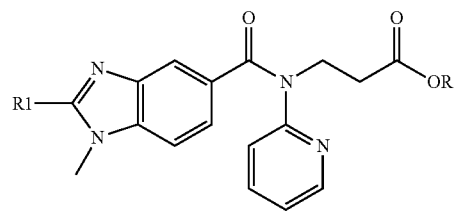

where R=—H or $C_1$-$C_5$ alkyl; and
$R_1$=—CHO or —$CH_3$, or —$CHX_2$, where X=—Cl, —Br, or —I.

In a preferred embodiment, in Formula II, when $R_1$=—CHO, R=—H, —$CH_3$ or —$C_2H_5$ In a preferred embodiment, in Formula II, when $R_1$=—$CHCl_2$, R=—H, —$CH_3$ or —$C_2H_5$ In a preferred embodiment, in Formula II, when $R_1$=—$CH_3$, R=—H, —$CH_3$ or —$C_2H_5$ Preferably, the compound is selected from the group consisting of Ethyl-3-{[(2-dichloromethyl-1-methyl-1H-benzimidazole-5-yl)carbonyl]-(2-pyridinyl)amino}propanoate; Ethyl-3-{[(2-formyl-1-methyl-1H-benzimidazole-5-yl)carbonyl]-(2-pyridinyl)amino}propanoate; 3-{[(2-dichloromethyl-1-methyl-1H-benzimidazole-5-yl)carbonyl]-(2-pyridinyl)amino}propanoic acid and 3-{[(2-formyl-1-methyl-1H-benzimidazole-5-yl)carbonyl]-(2-pyridinyl)amino}propanoic acid.

Preferably, the compound is selected from the group consisting of, Methyl-3-{[(2-dichloromethyl-1-methyl-1H-benzimidazole-5-yl)carbonyl]-(2-pyridinyl)amino}propanoate; Methyl-3-{[(2-formyl-1-methyl-1H-benzimidazole-5-yl)carbonyl]-(2-pyridinyl)amino}propanoate; Ethyl-3-{[(1,2-dimethyl-1H-benzimidazol-5-yl)carbonyl]-(2-pyridinyl)amino}propanoate; Methyl-3-{[(1,2-dimethyl-1H-benzimidazol-5-yl)carbonyl]-(2-pyridinyl)amino}propanoate and 3-{[(1,2-dimethyl-1H-benzimidazol-5-yl)carbonyl]-(2-pyridinyl)amino}propanoic acid.

Compounds as defined above are used in the preparation of Dabigatran etexilate.

Prior art discloses the use of Ethyl-3-{[(2-hydroxymethyl-1-methyl-1H-benzimidazole-5-yl)carbonyl]-(2-pyridinyl)amino}propanoate or Ethyl-3-{[(2-halomethyl-1-methyl-1H-benzimidazole-5-yl)carbonyl]-(2-pyridinyl)amino}propanoate as an intermediate for the preparation of Dabigatran etexilate or pharmaceutically acceptable salt thereof. It was found by the inventors of the present invention that use of Ethyl-3-{[(2-halomethyl-1-methyl-1H-benzimidazole-5-yl)carbonyl]-(2-pyridinyl)amino}propanoate for the preparation of Dabigatran etexilate did not provide the final product in the desired yield and purity. Further, it was found that the reaction did not proceed to completion.

Ethyl-3-{[(2-hydroxymethyl-1-methyl-1H-benzimidazole-5-yl)carbonyl]-(2-pyridinyl) amino}propanoate is not commercially available. Preparation of Ethyl-3-{[(2-hydroxymethyl-1-methyl-1H-benzimidazole-5-yl)carbonyl]-(2-pyridinyl)amino}propanoate from Ethyl-3-[(3-amino-4-methyl amino benzoyl)-N-(pyridin-2-yl)-amino]propanoate provided Ethyl-3-{[(2-hydroxymethyl-1-methyl-1H-benzimidazole-5-yl)carbonyl]-(2-pyridinyl)amino}propanoate in only about 50% yield thereby affecting the yield of the final product, hence the process is not cost effective.

The present invention uses a novel compound, in particular Ethyl-3-{[(2-formyl-1-methyl-1H-benzimidazole-5-yl)carbonyl]-(2-pyridinyl)amino}propanoate (IIA) for the preparation of Dabigatran etexilate. The preparation of Dabigatran etexilate using this novel compound was found to proceed smoothly in about 2 to 3 hours. Further, the condensation and reduction reaction is carried out in situ.

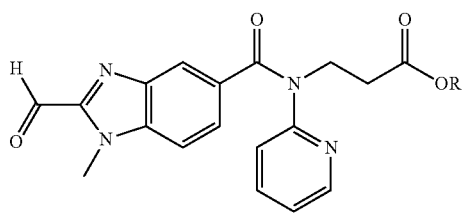

where R=H or —C₂H₅

Preferably, 1-methyl-2-[N-[4-amidinophenyl]aminomethyl]benzimidazol-5-yl-carboxylic acid-N-(2-pyridyl)-N-(2-ethoxycarbonylethyl)amide is purified by conversion to its acid addition salt. The acid treatment removes majority of the impurities, thereby improving the quality of the product. Acid used for purification is selected from methanesulfonic acid, ethanesulfonic acid, p-toluene sulfonic acid, oxalic acid, tartaric acid, citric acid or the like, preferably, methanesulfonic acid or p-toluene sulfonic acid.

Use of novel intermediate, Ethyl-3-{[(2-formyl-1-methyl-1H-benzimidazole-5-yl)carbonyl]-(2-pyridinyl)amino}propanoate increases the yield of the final product whereas the acid treatment for purification of 1-methyl-2-[N-[4-amidinophenyl]aminomethyl]benzimidazol-5-yl-carboxylic acid-N-(2-pyridyl)-N-(2-ethoxy carbonyl ethyl)amide increases the purity of the final product thereby making the process cost effective and industrially viable. By this process, 1-methyl-2-[N-[4-amidinophenyl]aminomethyl]benzimidazol-5-yl-carboxylic acid-N-(2-pyridyl)-N-(2-ethoxy carbonyl ethyl)amide is obtained in an yield of about 70 to 80% and purity of more than 95%.

Another embodiment of the present invention provides a process for the preparation of Ethyl-3-{[(2-formyl-1-methyl-1H-benzimidazole-5-yl)carbonyl]-(2-pyridinyl)amino}propanoate by reacting 2-formyl-1-methyl-1H-benzimidazole-5-carboxylic acid with Ethyl-3-[N-(2-pyridinyl)-amino]propanoate in presence of a halogenating agent selected from thionyl chloride, phosphorus trichloride or phosphorus pentachloride, preferably, thionyl chloride to obtain Ethyl-3-{[(2-formyl-1-methyl-1H-benzimidazole-5-yl)carbonyl]-(2-pyridinyl)amino}propanoate.

Another embodiment of the present invention provides a process for preparation of 2-formyl-1-methyl-1H-benzimidazole-5-carboxylic acid comprising treating 3-amino-4-(methylamino)benzoic acid or esters thereof with acetic acid derivative to obtain 2-formyl-1-methyl-1H-benzimidazole-5-carboxylic acid.

Another embodiment of the present invention provides 2-formyl-1-methyl-1H-benzimidazole-5-carboxylic acid and esters thereof.

Acetic acid derivative is selected from dihaloacetyl halide, dihaloacetic acid, dihaloacetic anhydride, glycolic acid, acetic acid, acetic anhydride, acetyl halide or glyoxylic acid. The halide is selected from chloro, bromo or iodo, preferably, chloro.

In a preferred embodiment, 3-amino-4-(methylamino) benzoic acid is suspended in a solvent selected from ethyl acetate, butyl acetate or tetrahydrofuran, preferably ethyl acetate at a temperature of about 10 to 30° C., preferably at 20° C. Dichloroacetyl chloride is added to the suspension and heated at a temperature of about 60 to 70° C., preferably at 65° C. for a period of 1 to 3 hours, preferably for 2 hours followed by addition of base selected from potassium carbonate, sodium carbonate, sodium bicarbonate, potassium bicarbonate, sodium hydroxide, potassium hydroxide or the like at 30 to 50° C. to obtain a mixture. The mixture is stirred further for about 1 hour. This mixture is filtered and the filtrate is washed with solvent selected from ethyl acetate, methyl acetate or butyl acetate, preferably ethyl acetate. The filtrate is concentrated to reduce the volume followed by treatment with a solvent selected from dimethyl sulfoxide, dimethyl formamide, dimethyl acetamide, acetonitrile, acetone, tetrahydrofuran, ethyl acetate or methyl acetate. The mixture is cooled and filtered. The solid obtained is washed with solvent selected from dimethyl sulfoxide, dimethyl formamide, dimethyl acetamide, acetonitrile, acetone, tetrahydrofuran, ethyl acetate, methyl acetate or mixture thereof to obtain a wet cake. The obtained wet cake is dried to obtain 2-dichloromethyl-1-methyl-1H-benzimidazole-5-carboxylic acid.

Scheme 6

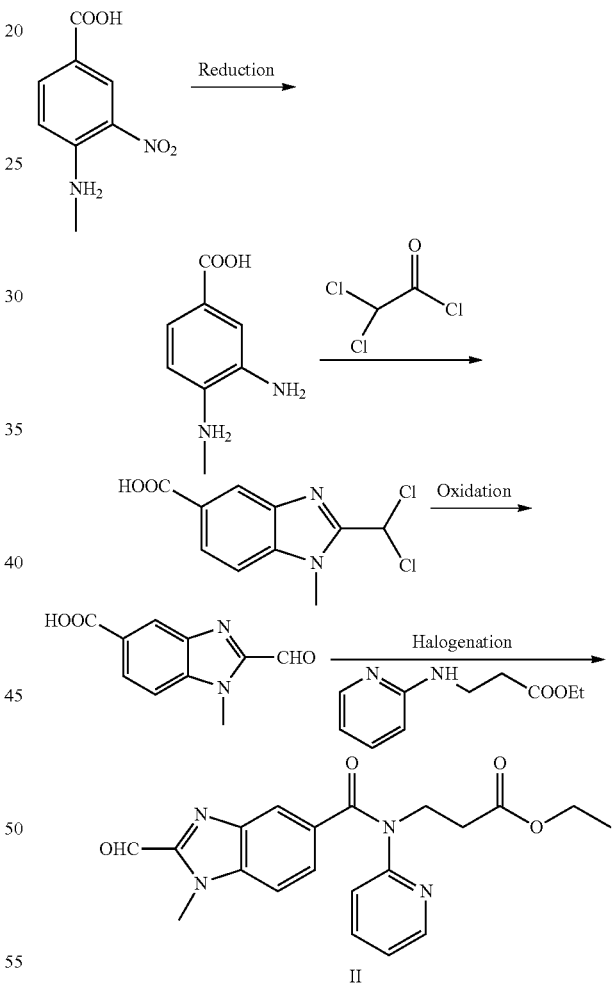

II

The obtained 2-dichloromethyl-1-methyl-1H-benzimidazole-5-carboxylic acid is subjected to oxidation using DMSO-base, sodium metaperiodate (NaIO4)-DMF or the like to obtain 2-formyl-1-methyl-1H-benzimidazole-5-carboxylic acid. The process is represented in Scheme 6 above.

In a preferred embodiment, 3-amino-4-(methylamino) benzoic acid is treated with glycolic acid under reflux in presence of solvent selected from toluene, xylene, heptane, cyclohexane or methyltert-butyl ether, preferably toluene. The reaction mixture is stirred at the same temperature for 18 to 25 hours, preferably for 20 to 22 hours. After completion of reaction, the mixture is cooled to 40 to 60° C., preferably 50 to 55° C. followed by concentration under vacuum to obtain an oil. The oil is dissolved in a solvent selected from dichloromethane, dichloroethane, chloroform or carbon tetrachloride, preferably dichloromethane. The organic layer is extracted with saturated sodium bicarbonate solution followed by water. The organic layer is separated and concentrated to obtain a residue. The residue is treated with solvent selected from hexane, pentane, cyclopentane, cyclohexane, toluene or xylene, preferably hexane to obtained a slurry. The obtained slurry is stirred for ½ hour to 1 hour at ambient temperature. The slurry is filtered and the solid obtained is washed with hexane. The wet cake obtained is dissolved in solvent selected from acetonitrile, acetone, tetrahydrofuran (THF), ethyl acetate, methyl acetate, dimethyl formamide, dimethylacetamide or dimethyl sulfoxide (DMSO), preferably acetonitrile at 40 to 60° C., preferably at 45 to 50° C. to obtain a solution. The solution is cooled and maintained under stirring to obtain a slurry. The slurry is filtered and the obtained solid is washed and dried to obtain 2-hydroxymethyl-1-methyl-1H-benzimidazole-5-carboxylic acid.

manganese dioxide, Dess-Martin periodinane or pyridinium chloroformate, preferably manganese, dioxide in presence of solvent selected from dichloromethane, dichloroethane, chloroform, carbon tetrachloride, THF, methyl-THF, 1,4-dioxane or toluene, preferably dichloromethane to obtain a mixture. The resultant mixture is stirred at 25 to 30° C. for 20 to 30 hours, preferably for 24 hours. The reaction mixture is filtered and the obtained solid is washed with solvent selected from dichloromethane, dichloroethane, chloroform or carbon tetrachloride, preferably dichloromethane. The filtrate is concentrated under vacuum to obtain a solid. The obtained solid is treated with solvent selected from hexane, heptane, pentane or toluene and the obtained slurry is filtered to obtain 2-formyl-1-methyl-1H-benzimidazole-5-carboxylic acid. The process is represented in Scheme 7 above.

Yet another preferred embodiment provides a process for preparation of 2-formyl-1-methyl-1H-benzimidazole-5-carboxylic acid by treating 3-amino-4-(methylamino)benzoic acid with glyoxylic acid in presence of solvent selected from xylene, heptane, cyclohexane or methyltert-butyl ether at reflux temperature to obtain 2-formyl-1-methyl-1H-benzimidazole-5-carboxylic acid. The process is represented in Scheme 8 below,

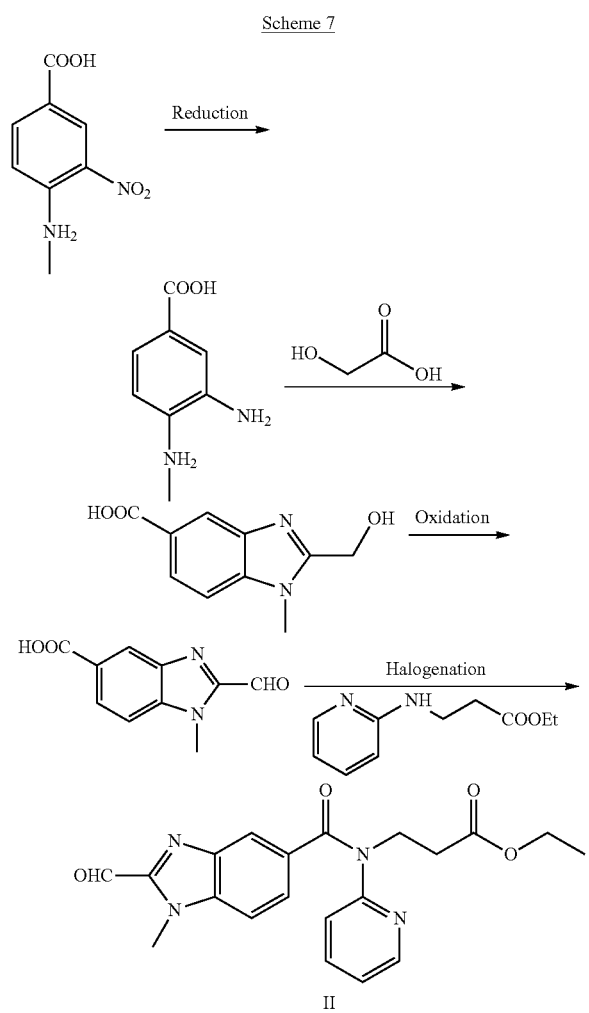

2-hydroxymethyl-1-methyl-1H-benzimidazole-5-carboxylic acid is treated with an oxidizing agent selected from

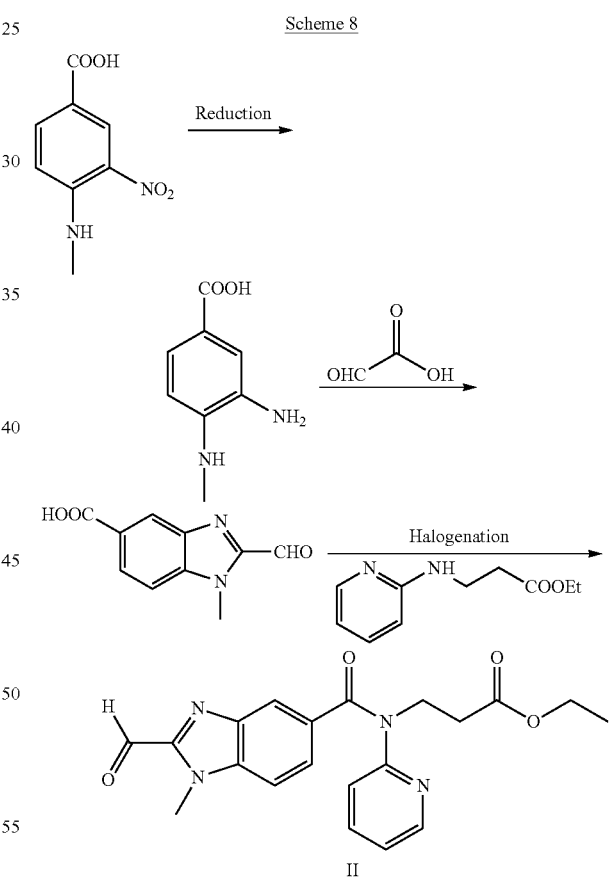

Alternatively, 3-amino-4-(methylamino)benzoate is treated with acetic acid or acetyl chloride or acetic anhydride to obtain 1,2-dimethyl-1H-benzimidazole-5-carboxylate; subjecting 1,2-dimethyl-1H-benzimidazole-5-carboxylate to oxidation and further hydrolysis to obtain 2-formyl-1-methyl-1H-benzimidazole-5-carboxylic acid;

Another embodiment of the present invention provides 1,2-dimethyl-1H-benzimidazole-5-carboxylic acid and ester thereof.

3-amino-4-(methylamino)benzoic acid esters can be used in place of 3-amino-4-(methylamino)benzoic acid. Preferably, alkyl ester such as methyl ester or ethyl ester is used. 3-nitro-4-(methylamino)benzoic acid is subjected to esterification and reduction reaction to obtain 3-amino-4-(methylamino)benzoic acid esters. Preferably, reduction is carried out using hydrogen gas in presence of catalyst selected from palladium/carbon, platinum/carbon or oxides thereof supported on various supports such as carbon, alumina and the like.

An alternate embodiment of the present invention provides a process for preparation of Dabigatran etexilate or pharmaceutically acceptable salt thereof comprising the steps of,
a) coupling Ethyl-3-[(3-amino-4-methylaminobenzoyl)-N-(pyridin-2-yl)-amino]propanoate with [(4-{[(hexyloxy)carbonyl]carbamimidoyl}phenyl)amino]acetic acid to obtain Dabigatran etexilate; and
b) optionally converting Dabigatran etexilate to its pharmaceutically acceptable salt.

Another embodiment of the present invention provides a process for preparation of Dabigatran etexilate or pharmaceutically acceptable salt thereof comprising the steps of,
a) reacting 4-amino benzonitrile with halo acetic acid alkyl ester to obtain N-(4-cyanophenyl)glycine alkyl ester;
b) subjecting N-(4-cyanophenyl)glycine alkyl ester to Pinner reaction in presence of alcohol, acid and base to obtain (4-amidinophenyl)glycine alkyl ester;
c) reacting (4-amidinophenyl)glycine alkyl ester with n-hexyl chloroformate followed by hydrolysis to obtain [(4-{[(hexyloxy)carbonyl]carbamimidoyl}phenyl)amino]acetic acid;
d) converting [(4-{[(hexyloxy)carbonyl]carbamimidoyl}phenyl)amino]acetic acid to Dabigatran etexilate or its pharmaceutically acceptable salt.

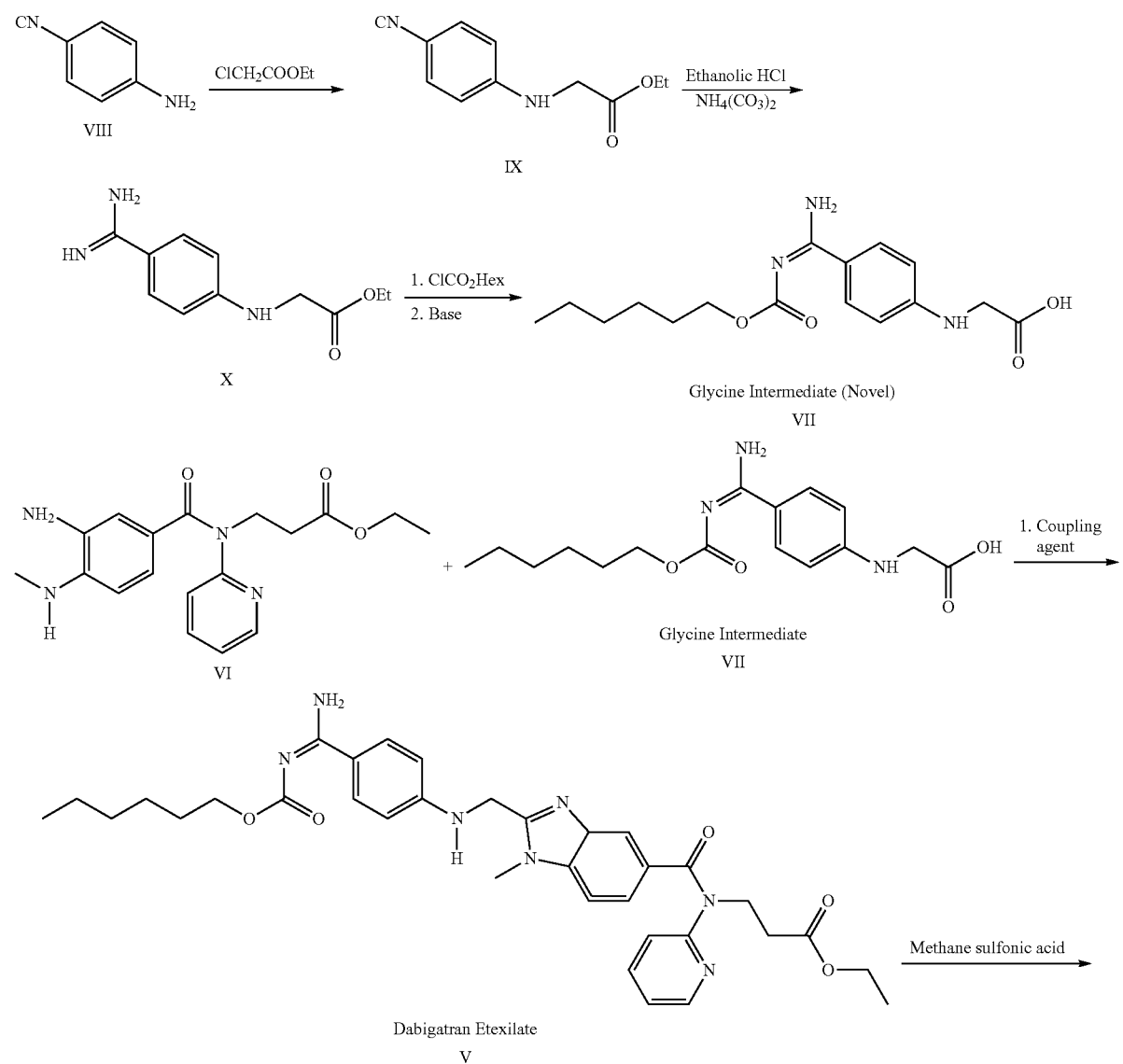

Scheme 9

-continued

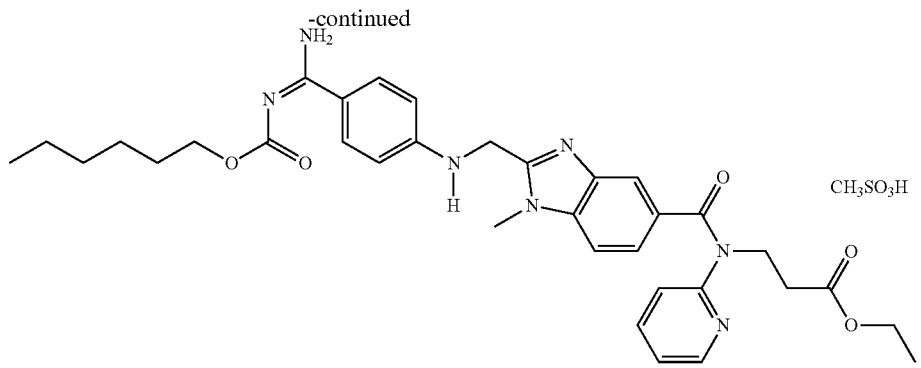

Dabigatran Etexilate Mecylate

I

Another embodiment of the present invention provides a novel Glycine intermediate of formula VII, [(4-{[(hexyloxy)carbonyl]carbamimidoyl}phenyl)amino]acetic acid and esters thereof.

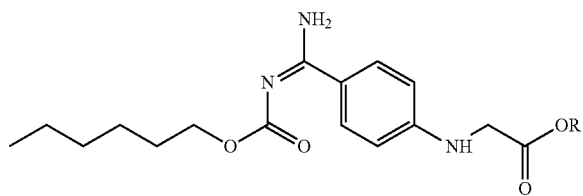

where R=H or $C_1$-$C_3$alkyl

In a preferred embodiment, 4-aminobenzonitrile is treated with halo acetic acid alkyl ester, preferably ethyl chloroacetate in presence of solvent selected from ethyl acetate, butyl acetate, methyl acetate, tetrahydrofuran or 1,4 dioxane, preferably ethyl acetate at reflux temperature to obtain N-(4-cyanophenyl)glycine ethyl ester. N-(4-cyanophenyl) glycine ethyl ester is subjected to Pinner reaction in presence of alcohol selected from $C_1$-$C_4$ alcohol such as ethanol, methanol or isopropyl alcohol, preferably ethanol; acid selected from HCl, HBr, $H_2SO_4$ or the like and base selected from ammonia, ammonium hydroxide, ammonium carbonate, primary amines or secondary amines to obtain (4-amidinophenyl)glycine ethyl ester. The obtained (4-amidino phenyl)glycine ethyl ester is reacted with alkylating agent such as n-hexyl chloroformate in presence of base selected from potassium carbonate, sodium carbonate, lithium carbonate, cesium carbonate, sodium bicarbonate, or potassium bicarbonate, followed by hydrolysis using strong bases such as sodium hydroxide, potassium hydroxide or lithium hydroxide, preferably lithium hydroxide to get [(4-{[(hexyloxy)carbonyl]carbamimidoyl}phenyl)amino]acetic acid.

[(4-{[(hexyloxy)carbonyl]carbamimidoyl}phenyl)amino] acetic acid is coupled with Ethyl-3-[(3-amino-4-methylaminobenzoyl)-N-(pyridin-2-yl)-amino]propanoate in presence of coupling agent such as pivaloyl chloride, isobutyl chloroformate, propane phosphinic anhydride, 1,1'-carbodiimidazole (CDI), 1-Ethyl-3-(3-dimethylamino propyl)carbodiimide hydrochloride (EDC.HCl), Diisopropyl carbodiimide (DIC) or Dicyclohexyl carbodiimide (DCC) and solvent selected from dichloromethane, dichloroethane, chloroform, carbon tetrachloride, THF, Methyl-THF, 1,4-dioxane or toluene, preferably dichloromethane followed by treatment with acid selected from formic acid, acetic acid, methanesulfonic acid, p-toluenesulfonic acid, HCl or sulfuric acid, preferably acetic acid to obtain Dabigatran etexilate. Dabigatran etexilate thus obtained is further converted to Dabigatran etexilate mesylate by treating Dabigatran etexilate with methane sulfonic acid. The process is represented in Scheme 9 above.

Ethyl-3-[(3-amino-4-methylaminobenzoyl)-N-(pyridin-2-yl)-amino]propanoate, used in the process of the present invention can be prepared by any method known in the art. Ethyl-3-[(3-nitro-4-methylaminobenzoyl)-N-(pyridin-2-yl)-amino]propanoate is subjected to hydrogenation in the presence of catalyst selected from Raney-nickel, palladium/carbon or platinum/carbon, preferably Raney-nickel and solvent selected from ethyl acetate, butyl acetate, methyl acetate, tetrahydrofuran or 1,4-dioxane, preferably ethyl acetate at ambient temperature. The catalyst is filtered off and the filtrate is evaporated to obtain Ethyl-3-[(3-amino-4-methylaminobenzoyl)-N-(pyridin-2-yl)-amino]propanoate.

In another embodiment, Ethyl-3-[(3-amino-4-methylaminobenzoyl)-N-(pyridin-2-yl)-amino]propanoate is reacted with N-(4-cyanophenyl)glycine in presence of coupling agent such as pivaloyl chloride, isobutyl chloroformate, propanephosphonic anhydride, 1,1'-carbodiimidazole (CDI), 1-Ethyl-3-(3-dimethylaminopropyl)carbodiimide hydrochloride (EDC.HCl), Diisopropylcarbodiimide (DIC), Dicyclohexyl carbodiimide (DCC) and solvent selected from dichloromethane, dichloroethane, chloroform, carbon tetrachloride, THF, Methyl-THF, 1,4-dioxane or toluene, preferably dichloromethane followed by treatment with acid selected from formic acid, acetic acid, methanesulfonic acid, p-toluenesulfonic acid, HCl or sulfuric acid, preferably, acetic acid at reflux to obtain a mixture. The mixture is refluxed for a period of five hours. The solvent is distilled off and the residue is extracted with a solvent selected from dichloromethane, dichloroethane or chloroform. The organic extract is washed with sodium bicarbonate solution followed by water and dried over sodium sulfate. The organic layer is evaporated so as to obtain 1-methyl-2-[N-(4-cyanophenyl)-aminomethyl]-benzimidazole-5-yl-carboxylicacid-N-(2-pyridinyl)-N-(2-ethoxycarbonylethyl)-amide.

1-methyl-2-[N-(4-cyanophenyl)-aminomethyl]-benzimidazole-5-yl-carboxylicacid-N-(2-pyridinyl)-N-(2-ethoxycarbonylethyl)-amide is further subjected to Pinner reaction in presence of alcohol selected from $C_1$-$C_4$ alcohol such as ethanol, methanol or isopropyl alcohol, preferably ethanol;

acid selected from HCl, HBr, $H_2SO_4$ or the like and base selected from ammonia, ammonium hydroxide, ammonium carbonate, primary amines or secondary amines to obtain an oily residue. The oily residue is treated with solvent selected from ethyl acetate, butyl acetate, methyl acetate, tetrahydrofuran, 1,4-dioxane, ethanol, methanol, isopropanol or mixture thereof to obtain a semisolid containing 1-methyl-2-[N-(4-amidinophenyl)-aminomethyl]-benzimidazole-5-yl-carboxylic acid-N-(2-pyridinyl)-N-(2-ethoxycarbonyl ethyl)-amide along with impurities such as ammonium salts. The obtained semisolid product is further dissolved in solvent selected from ethanol, methanol or isopropanol followed by addition of sodium acetate. The mixture is further treated with acid such as methanesulphonic acid to obtain 1-methyl-2-[N-(4-amidinophenyl)-aminomethyl]-benzimidazole-5-yl-carboxylic acid-N-(2-pyridinyl)-N-(2-ethoxycarbonylethyl)-amide mesylate. The obtained 1-methyl-2-[N-[4-amidinophenyl]aminomethyl]benzimidazol-5-yl-carboxylic acid-N-(2-pyridinyl)-N-(2-ethoxycarbonylethyl)amide mesylate is reacted with an alkylating agent such as n-hexyl chloroformate in presence of base selected potassium carbonate, sodium carbonate, lithium carbonate, cesium carbonate, sodium bicarbonate, potassium bicarbonate, triethyl amine or N-methyl morpholine and solvent selected from tetrahydrofuran (THF), 1,4-dioxane, diethyl ether, diisopropyl ether, methyl tertiary butyl ether or 1,4-dioxane, preferably tetrahydrofuran (THF) at ambient temperature to obtain a mixture. The mixture is stirred for 1 to 3 hours, preferably for 2 hours and the solvent is distilled off. The residue is treated with saturated saline solution and solvent such as dichloromethane. The organic extract is dried over sodium sulfate and concentrated. The product, obtained is further purified using solvent selected from $C_1$-$C_4$ alcohol such as isopropyl alcohol, methanol or ethanol, preferably isopropyl alcohol (IPA) to obtain Dabigatran etexilate. The Dabigatran etexilate is further converted to Dagibatran etexilate mesylate by treating the Dabigatran etexilate with methane sulfonic acid.

Another embodiment of the present invention provides conversion of 1-methyl-2-[N-[4-amidinophenyl]aminomethyl]benzimidazol-5-yl-carboxylic acid-N-(2-pyridyl)-N-(2-ethoxycarbonylethyl)amide to Dabigatran etexilate mesylate (I) comprising treating 1-methyl-2-[N-[4-amidinophenyl]aminomethyl]benzimidazol-5-yl-carboxylic acid-N-(2-pyridyl)-N-(2-ethoxycarbonylethyl)amide with an alkylating agent such as n-hexyl chloroformate in presence of base selected sodium carbonate, potassium carbonate, lithium carbonate, cesium carbonate, sodium bicarbonate, potassium bicarbonate, triethyl amine or N-methyl morpholine to obtain Dabigatran etexilate or pharmaceutically acceptable salt thereof.

Solvent for the above reaction is selected from acetone, methyl ethyl ketone, methyl isobutyl ketone, ethanol, methanol, isopropanol, butanol, ethyl acetate, methyl acetate or mixture thereof.

Another embodiment of the present invention provides the conversion of Dabigatran etexilate to Dabigatran etexilate mesylate comprising the steps of,
  a) treating Dabigatran etexilate in a solvent to obtain a clear solution;
  b) adding methane sulfonic acid to the clear solution obtained in step a) to obtain a slurry; and
  c) isolating Dabigatran etexilate mesylate In a preferred embodiment, Ethyl-3-{[(2-{[(4-{N'-[(hexyloxycarbonyl]-carbamimidoyl}-phenyl)amino]methyl}-1-methyl-1H-benzimidazole-5-yl)carbonyl]-(2-pyridinyl)amino}propanoate is dissolved in a solvent selected from acetone, acetonitrile, tetrahydrofuran, ethyl acetate, methyl acetate, dimethyl formamide, dimethyl acetamide or dimethyl sulfoxide at 20 to 40° C., preferably at 25 to 30° C. to obtain a mixture. The mixture is warmed to 30 to 50° C., preferably at 40 to 45° C. to obtain a clear solution. The solution is further cooled to 25 to 30° C. followed by addition of methanesulfonic acid dissolved in solvent selected from acetone, acetonitrile, tetrahydrofuran, ethyl acetate, methyl acetate, dimethyl formamide, dimethyl acetamide or dimethyl sulfoxide, preferably acetone over a period of 5 to 10 minutes. The solution is maintained under stirring for 3 to 5 hours, preferably for 4 hours at 25 to 30° C. to obtain a slurry. The slurry is filtered to obtain a solid. The solid is washed with acetone and dried to obtain Dabigatran etexilate mesylate. Dabigatran etexilate mesylate obtained by the process of the present invention is substantially pure.

Another embodiment of the present invention provides a process for preparation of Dabigatran etexilate mesylate comprising the steps of,
  a) reacting 1-methyl-2-[N[4-amidinophenyl]aminomethyl]benzimidazol-5-yl-carboxylic acid-N-(2-pyridyl)-N-(2-ethoxycarbonylethyl)amide or mesylate thereof with n-hexyl chloroformate to obtain Dabigatran etexilate tetrahydrate;
  b) optionally purifying Dabigatran etexilate tetrahydrate;
  c) converting Dabigatran etexilate tetrahydrate to Dabigatran etexilate anhydrous; and
  d) converting Dabigatran etexilate anhydrous to Dabigatran etexilate mesylate Form I.

Preferably, Dabigatran etexilate anhydrous is polymorphic Form I. Preferably, Dabigatran etexilate mesylate is polymorphic Form I.

In a preferred embodiment, 1-methyl-2-[N-[4-amidinophenyl]aminomethyl]benzimidazol-5-yl-carboxylic acid-N-(2-pyridyl)-N-(2-ethoxycarbonylethyl)amide mesylate is reacted with n-hexyl chloroformate in presence of base selected from sodium carbonate, potassium carbonate, lithium carbonate, cesium carbonate, sodium bicarbonate, potassium bicarbonate, triethyl amine or N-methyl morpholine and solvent selected from acetone, methyl ethyl ketone, methyl isobutyl ketone, ethanol, methanol, isopropanol, butanol, ethyl acetate, methyl acetate, water or mixture thereof at temperature of about 5 to 25° C., preferably 10 to 15° C. The mixture is stirred at the same temperature for about ½ hour to 1 hour. After the completion of the reaction, the reaction mixture is diluted with water to obtain a slurry. This slurry is maintained under stirring for about ½ hour to 1 hour at 10 to 30° C., preferably 15 to 20° C. The slurry is filtered and the solid obtained is washed and dried to obtain Dabigatran etexilate tetrahydrate.

Figure 3:
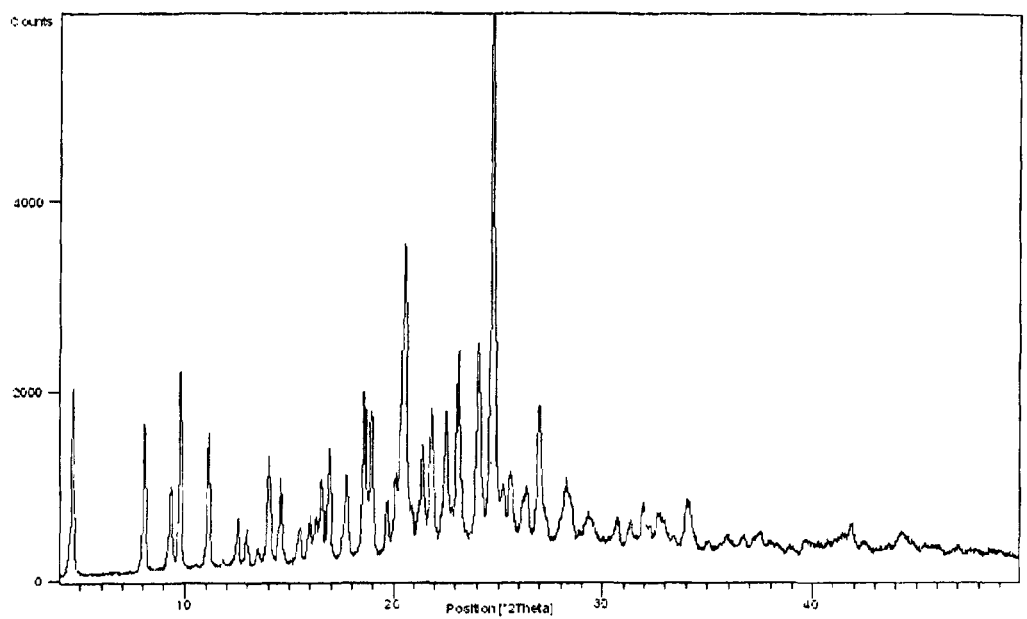
FIG. 3: X-ray powder diffraction pattern of Dabigatran etexilate tetrahydrate.

Dabigatran etexilate tetrahydrate thus obtained is taken in a solvent selected from ethyl acetate, methyl acetate or tert butyl acetate, preferably ethyl acetate at ambient temperature to obtain a mixture. This mixture is further treated with a solvent selected from cyclohexane, cyclopentane, hexane, heptane, pentane, toluene or xylene, preferably cyclohexane to obtained a slurry. The resultant slurry is heated at temperature of about 50 to 70° C., preferably at 60-65° C. followed by stirring for about ½ hour to 1 hour at the same temperature. The slurry is cooled to a temperature of about 10 to 30° C., preferably 20 to 25° C. and stirred for 1 to 3 hours, preferably for 2 hours. The slurry is filtered and the solid obtained is washed and dried to obtain pure Dabigatran etexilate tetrahydrate. Dabigatran etexilate tetrahydrate obtained by the present invention is characterized by X-ray powder diffraction pattern as shown in FIG. 3.

Figure 4:
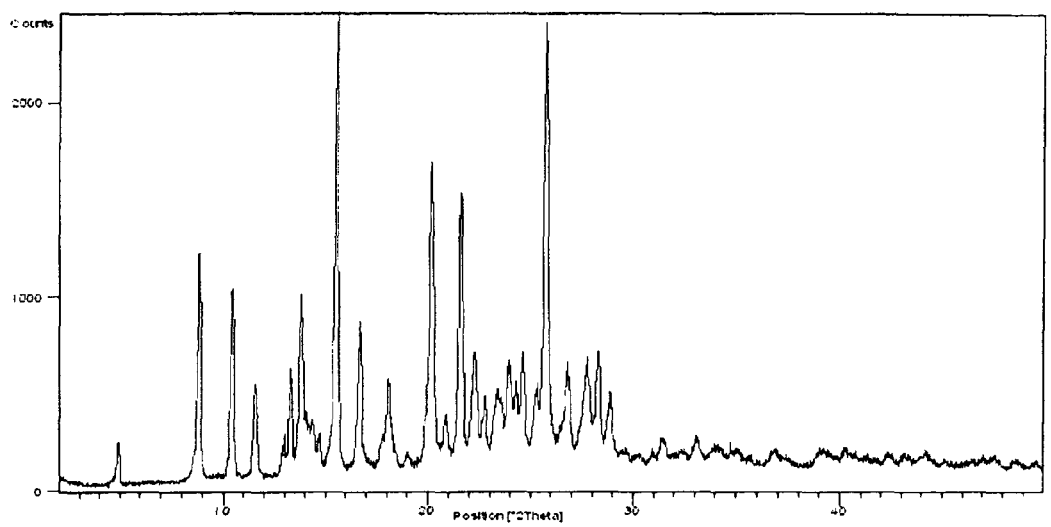
FIG. 4: X-ray powder diffraction pattern of Dabigatran etexilate Form I.

Dabigatran etexilate tetrahydrate is converted to Dabigatran etexilate anhydrous Form I by dissolving pure Dabigatran etexilate tetrahydrate in a solvent selected from ethyl acetate, methyl acetate, propyl acetate or butyl acetate, preferably ethyl acetate at reflux temperature to obtain a solution. The solution is cooled to 20 to 40° C., preferably 25 to 30° C. The solution is maintained under stirring for about 3 to 6 hours, preferably for 4 hours at the same temperature to obtain a slurry. The slurry is filtered and the solid obtained is washed with an organic solvent and dried to obtain Dabigatran etexilate anhydrous Form I, characterized by X-ray powder diffraction pattern as shown in FIG. 4.

Dabigatran etexilate anhydrous Form I is treated with methane sulfonic acid in acetone to obtain Dabigatran etexilate mesylate Form I, characterized by X-ray powder diffraction pattern as shown in FIG. 1.

In an alternate embodiment, Dabigatran etexilate tetrahydrate is converted to

Dabigatran etexilate mesylate by a process comprising the steps of,
   a) obtaining a solution of Dabigatran etexilate tetrahydrate;
   b) optionally, filtering the solution obtained in step a);
   c) adding the obtained solution of step a) or step b) to a solution of methane sulfonic acid to obtain a mixture; and
   d) isolating Dabigatran Etexilate Mesylate from the mixture of step c).

Solvent is selected from ethyl acetate, methyl acetate, acetone, methyl ethyl ketone, acetonitrile, methanol, ethanol, dimethylformamide or dimethylacetamide, preferably ethyl acetate. It has been observed by the inventors of the present invention that addition of a solution of Dabigatran etexilate to a solution of methane sulfonic acid helps in controlling the formation of impurities.

Figure 2:
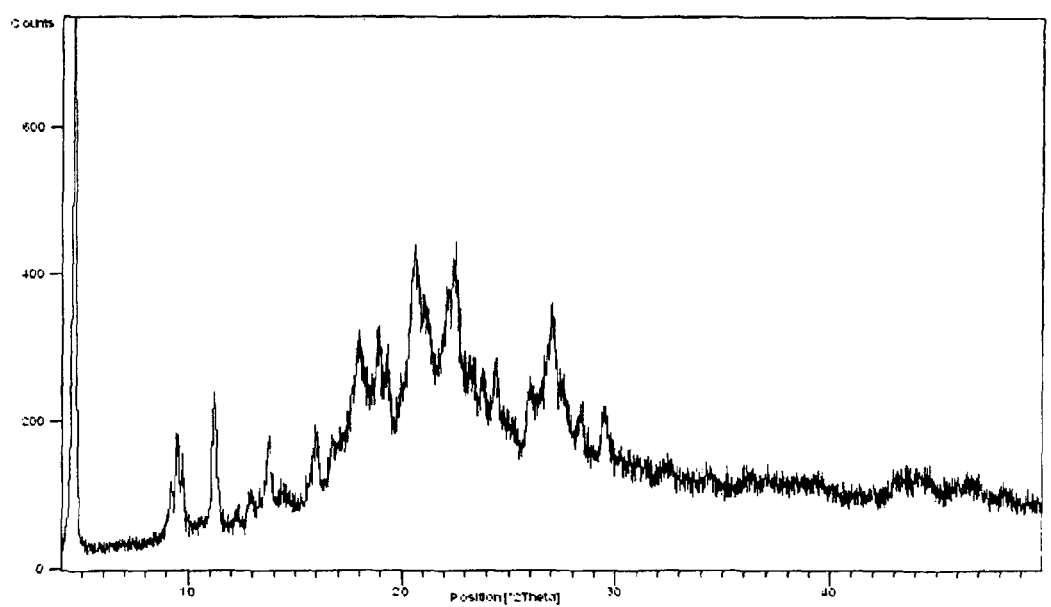
FIG. 2: X-ray powder diffraction pattern of Dabigatran etexilate mesylate Form I.

In a preferred embodiment, a solution of Dabigatran etexilate tetrahydrate is obtained by treating Dabigatran etexilate tetrahydrate with ethyl acetate at a temperature of 45-65° C., preferably 55-60° C. This warm solution is filtered and added to a solution of methanesulfonic acid in ethyl acetate at the same temperature. The mixture is maintained at the same temperature for about half an hour. The solid obtained is filtered and dried to obtain Dabigatran etexilate mesylate Form I, characterized by X-ray powder diffraction pattern as shown in FIG. 2. It is further characterized by peaks expressed as 2-theta values at about 4.64, 9.41, 11.17, 13.70, 15.92, 17.90, 18.84, 20.48, 22.44, 24.37, 27.02 and 29.42 degrees.

Dabigatran etexilate mesylate obtained according to present invention is substantially pure and has chemical purity of more than 99.5% with all impurities below 0.15%, preferably below 0.1%.

Another embodiment of the present invention provides a process for preparation of 4-aminobenzamidine, comprising treating 4-aminobenzonitrile with hydroxylamine to obtain the corresponding oxime. The oxime thus obtained is subjected to reduction to obtain 4-aminobenzamidine.

Another embodiment of the present invention provides pharmaceutical composition comprising Dabigatran etexilate mesylate, prepared by the process of the present invention. Dabigatran etexilate mesylate, obtained by the process of the present invention, may be combined with pharmaceutically acceptable excipients to obtain suitable pharmaceutical compositions, used to reduce the risk of stroke and systemic embolism in patients with non-valvular atrial fibrillation.

Advantages of the process of the present invention:
1. Process of the present invention is simple, cost-effective, high yielding and industrially viable;
2. Dabigatran etexilate obtained by the process of the present invention is substantially pure with all impurities below 0.15%, preferably below 0.1%;
3. Reaction time is less as compared to prior art processes;
4. Reaction can be carried at ambient temperature.

Unless otherwise indicated, the following definitions are set forth to illustrate and define the meaning and scope of the various terms used to describe the invention herein.

The term "substantially pure" means Dabigatran etexilate or pharmaceutically acceptable salt thereof having less than about 1.%, preferably less than about 0.5%, more preferably less than about 0.3%, most preferably less than about 0.15% of undesired compounds including other polymorphic forms.

The term "reflux temperature" means the temperature at which the solvent or solvent system refluxes or boils at atmospheric pressure.

The term "ambient temperature" means the temperature in the range of 20 to 30° C., preferably 25 to 30° C.

The term "pharmaceutically acceptable" means that which is useful in preparing a pharmaceutical composition, that which is generally non-toxic and is not biologically undesirable and includes that which is acceptable for human pharmaceutical use The following examples are for illustrative purposes only and are not intended to limit the scope of the invention in any way.

EXAMPLES

Example 1: Preparation of Ethyl-3-{[(2-formyl-1-methyl-1H-benzimidazole-5-yl)carbonyl]-(2-pyridinyl)amino}propanoate A) Ethyl-3-{[(2-dichloromethyl-1-methyl-1H-benzimidazole-5-yl)carbonyl]-(2-pyridinyl)amino}propanoate A mixture of Ethyl-3-[(3-amino-4-methylaminobenzoyl)-N-(2-pyridinyl)amino]propanoate (500 μm) and acetonitrile (2 L) was cooled to −15° C. To this cold suspension, was added a solution of dichloroacetyl chloride (226.25 gm) in acetonitrile (500 ml) by maintaining the temperature at −10 to −15° C. over a period of 2 hours. The reaction mass was maintained at the same temperature for 1 hour. The temperature of the reaction mass was raised to 25 to 35° C. The reaction mass was slowly heated to 50 to 60° C. and was maintained at same temperature till reaction completion was achieved. The reaction mass was cooled to 25 to 35° C. and was quenched in cold solution of sodium bicarbonate (153.49 μm). This mixture was stirred at 0 to 5° C. for 30 min. The precipitated white solid was filtered and the cake was washed with water. The solid was dried at 50 to 60° C. till constant weight was achieved. The solid was then suspended in isopropanol (3 vol) and heated to 50 to 60° C. for 30 min. The reaction mass was cooled to 25 to 35° C. The white solid obtained was filtered, washed with isopropanol (1 vol) and dried under vacuum. The solid was further dried in tray dryer at 50 to 60° C. till LOD complies.

Yield: 586.7 μm (98.8%); Purity: 95% by HPLC; (M+1): 435.4 & 437.5; (M+Na): 457.4 & 459.4

$^1$H NMR (400 MHz, DMSO-d6): 1.13 (t, 3H), 2.70 (t, 2H), 3.92 (s, 3H), 3.98 (m, 2H), 4.24 (t, 2H), 6.96-7.59 (Ar, 6H), 7.85 (s, 1H), 8.4 (d, 1H)

$^{13}$C NMR (400 MHz, DMSO-d6): 14.4, 31.28, 33.44, 44.86, 60.50, 63.51, 111.11, 121.05, 121.94, 122.62, 124.89, 131.16, 137.62, 138.53, 140.25, 149.22, 150.70, 156.25, 170.35, 171.48.

B) Ethyl-3-{-[(2-formyl-1-methyl-1H-benzimidazole-5-yl)carbonyl]-(2-pyridinyl)amino}propanoate To a mixture of Ethyl-3-{[(2-dichloromethyl-1-methyl-1H-benzimidazole-5-yl)carbonyl]-(2-pyridinyl)amino}propanoate (100 gm) in toluene was charged sodium acetate (38.66 gm) and tetrabutyl ammonium bromide (14.82 gm) as phase transfer catalyst. The reaction mixture was heated slowly to 90° C. and was maintained at the same temperature for 3 to 4 hours. Complete consumption of dichloro compound was checked by TLC. The light brown reaction mass was cooled to 60 to 70° C. and filtered through filter paper under suction. The clear filtrate was concentrated under vacuum at temperature below 60° C. to get light brown coloured oil (diacetate) (132 gm). To this oil, was charged an aqueous solution of sodium carbonate (48.71 gm) and tetrabutyl ammonium bromide (10 gm). The reaction mass was heated to 40° C. and was maintained under stirring at same temperature for 1 hour. The reaction mass was then maintained under stirring at ambient temperature for 4 to 6 hours. The precipitated solid was filtered and washed with 500 ml water in 5 equal lots. The solid was dried at 50 to 60° C. Yield 80 gm (91.58%); Purity: 95% by HPLC; (M+1): 381.7 Melting range: 129 to 132° C.;

$^{1}$H NMR (400 MHz, DMSO-d6): 1.13 (t, 3H), 2.72 (t, 2H), 4.00 (q, 2H), 4.04 (s, 3H), 4.25 (t, 2H), 7.00 (d, 1H), 7.15 (t, 1H), 7.42 (d, 1H), 7.58 (t, 1H), 7.66 (s, 1H), 7.67 (d, 1H), 8.40 (s, 1H), 9.97 (s, 1H)

$^{13}$CNMR (400 MHz, DMSO-d6): 13.86, 31.28, 32.83, 44.29, 59.93, 111.43, 121.47, 121.85, 122.02, 126.20, 131.41, 137.26, 138.01, 140.70, 147.37, 148.66, 155.60, 169.56, 170.90, 185.02.

Example 2: Preparation of Ethyl-3-{[(2-formyl-1-methyl-1H-benzimidazole-5-yl)carbonyl]-(2-pyridinyl)amino}propanoate A) Preparation of Ethyl-3-{[(2-hydroxymethyl-1-methyl-1H-benzimidazole-5-yl)carbonyl]-(2-pyridinyl)amino}propanoate In a 3 liter RB flask equipped with a mechanical stirrer and Dean Stark apparatus were taken toluene (1500 ml) and Ethyl-3-[(3-amino-4-methylaminobenzoyl)-N-(2 pyridinyl)amino]propanoate (100 g). To this mixture, Glycolic acid (33 gm) was charged at 25 to 28° C. and this mixture was heated to 110-115° C. The mixture was stirred at the same temperature for 20 to 22 hours. After the completion of reaction, the mixture was cooled to 50-55° C. and concentrated under vacuum to obtain an oil. The oil was dissolved in Dichloromethane (1000 ml) and was extracted with saturated sodium bicarbonate solution (500 ml) followed by water (500 ml). The organic layer was separated and concentrated to obtain a residue. The residue was treated with hexane (1500 ml) and the resultant slurry was stirred for 1 hour at ambient temperature. The slurry was filtered to obtain a solid. The solid obtained was washed with hexane (200 ml). The wet cake (100 g, about 70% pure) was dissolved in acetonitrile (200 ml) at 45-50° C. The solution was cooled to ambient temperature to obtain a slurry. The slurry was cooled to 10-15° C. and stirred for 1 hour. The slurry was filtered and the solid was washed with cold acetonitrile (2×25 ml) and air-dried. The product was further dried at 45-50° C. for 6-8 hours.

Yield: 50 g (45%); Purity: more than 97%; Melting point 139-142° C.

B) Ethyl-3-{[(2-formyl-1-methyl-1H-benzimidazole-5-yl)carbonyl]-(2-pyridinyl) amino}propanoate In a 2 liter RB flask equipped with a mechanical stirrer, dichloromethane (750 ml) and Ethyl-3-{[(2-hydroxymethyl-1-methyl-1H-benzimidazole-5-yl)carbonyl]-(2-pyridinyl)amino}propanoate (50 g) were charged at 25-28° C. MnO$_2$ (50 g) was charged to this mixture at the same temperature. The mixture was stirred at ambient temperature for 24 hours. The mixture was filtered through hyflow bed and the residue was washed with dichloromethane (100 ml). The filtrate was concentrated under vacuum to obtain a solid. The solid was treated with hexane (200 ml) and the obtained slurry was stirred for 1 hour. The solid was filtered and air-dried to obtain the titled product.

Yield: 45 μm (90%); (M$^+$)=381.

$^{1}$H NMR (DMSO-d6): 9.97 (s, 1H), 8.4 (d, 2H), 7.57-7.86 (m, 3H), 7.40 (d, 2H), 7.14 (t, 1H), 4.2 (t, 3H), 4.0 (s, 1H), 3.95 (m, 2H), 2.7 (t, 2H), 1.15 (t, 3H);

$^{13}$C NMR (DMSO-d6): 185.59, 171.48, 156.17, 149.25, 138.58, 137.84, 131.99, 126.79, 122.60, 122.43, 122.04, 112.01, 60.51, 44.86, 33.41, 31.86 and 14.44.

Example 3: Preparation of Ethyl-3-{[(2-formyl-1-methyl-1H-benzimidazole-5-yl)carbonyl]-(2-pyridinyl)amino}propanoate A) Preparation of Ethyl-3-{[(1,2-dimethyl-1H-benzimidazol-5-yl)carbonyl]-(2-pyridinyl)amino}propanoate In a 2 liter flask equipped with a mechanical stirrer were taken acetic acid (500 ml) and Ethyl-3-[(3-amino-4-methylaminobenzoyl)-(pyridin-2-yl)-amino]propanoate (100 g). The mixture was heated to 115-120° C. The mixture was stirred at the same temperature for 5 to 6 hours. After completion of the reaction, the mixture was cooled to 50 to 55° C. and concentrated under vacuum to obtain a semisolid. To this semisolid, water (2000 ml) was added and the mixture was cooled to 10-15° C. The pH of this mixture was adjusted to 7 by addition of 7% sodium bicarbonate solution to obtain a slurry. The slurry thus obtained was stirred for 1 hour at 10-15° C. and filtered. The product obtained was washed with water (2×200 ml) and dried at 45-50° C.

Yield: 86 g; Purity: greater than 95%; m.p.: 177-179° C.; (M+1)=367

$^{1}$H NMR (DMSO-d6): 8.41 (m, 1H), 7.52-7.75 (m, 1H), 7.34-7.36 (m, 2H), 7.15 (m, 2H), 6.85-6.88 (d, 1H), 4.22 (t, 2H), 3.96-4.01 (q, 2H), 3.68 (s, 3H), 2.68 (t, 2H), 2.48 (s, 3H), 1.15 (t, 3H)

$^{13}$C NMR (DMSO-d6): 171.52, 170.94, 157.20, 154.37, 149.11, 141.68, 138.27, 131.46, 129.31, 122.62, 121.67, 119.31, 109.59, 60.47, 44.76, 33.52, 30.24, 14.44 and 13.88.

B) Preparation of Ethyl-3-{[(2-formyl-1-methyl-1H-benzimidazole-5-yl)carbonyl]-(2-pyridinyl)amino}propanoate In a 1 liter flask equipped with a mechanical stirrer, 1,4-dioxane (250 ml) and Ethyl-3-{[1,2-dimethyl-1H-benzimidazole-5-yl)carbonyl]-(2-pyridinyl)amino}propanoate (25 g) were charged at 25-28° C. SeO$_2$ (16.7 g) was charged to this mixture and the mixture was heated to 80-85° C. for 5-6 hours. The reaction mixture was cooled to 25-28° C. and filtered. The filtrate was concentrated under vacuum to obtain an oily mass. The oily mass was diluted with ethyl acetate (250 ml) and the mixture was filtered through hyflo. The filtrate was concentrated to obtain a residue and n-hexane (125 ml) was charged to this residue to obtain a slurry. The slurry was stirred for 1 hour and filtered. The product obtained was washed with n-hexane (50 ml) and air dried. The product was further dried at 45-50° C. Yield: 16 gm; (M+1)=381 $^1$H NMR (DMSO-d6): 9.97 (s, 1H), 8.41 (d, 2H), 7.57-7.86 (m, 3H), 7.40 (d, 2H), 7.14 (t, 1H), 4.20 (t, 3H), 4.01 (s, 1H), 3.95 (m, 2H), 2.70 (t, 2H), 1.15 (t, 3H)
$^{13}$C NMR (DMSO-d6): 185.59, 171.48, 156.17, 149.25, 138.58, 137.84, 131.99, 126.79, 122.60, 122.43, 122.04, 112.01, 60.51, 44.86, 33.41, 31.86 and 14.44

Example 4: Preparation of 1-methyl-2-[N-[4-amidinophenyl]aminomethyl]benzimidazol-5-yl-carboxylic acid-N-(2-pyridyl)-N-(2-ethoxycarbonylethyl) amide mesylate In a 1 liter RB flask equipped with a mechanical stirrer and addition funnel, acetic acid (500 ml) and Ethyl-3-{[(2-formyl-1-methyl-1H-benzimidazole-5-yl)carbonyl]-(2-pyridinyl)amino} propanoate (50 g) were charged at 25-28° C. 4-aminobenzamidine (28.3 g) was charged to the obtained mixture at the same temperature and the mixture was stirred for 2 hours. The mixture was cooled to 14-18° C. Sodium borohydride (5.5 g) was charged to this mixture in five lots. The reaction mixture was stirred at same temperature for 2 hours. The reaction mixture was concentrated under vacuum to obtain a semisolid residue. The residue was dissolved in ethanol (250 ml) at 55-60° C. and the solution was cooled to 25° C. Methanesulfonic acid (16.7 g) was added to this mixture over a period of 10-15 min. The mixture was diluted with acetone (200 ml) and stirred for 4-5 hours at ambient temperature. The slurry was filtered and the obtained solid was washed with acetone (2×50 ml). The solid was air dried and then dried at 45-50° C. to obtain titled product. Yield: 58 g (75%); Purity: more than 98%.

Example 5: Preparation of Dabigatran Etexilate

In a 1 liter RB flask equipped with a mechanical stirrer and addition funnel, water (125 ml) and potassium carbonate (23 gm) were charged at 25-28° C. Acetone (75 ml) and ethanol (75 ml) were charged at the same temperature. The mixture was cooled to 10-15° C. and to this was charged 1-methyl-2-[N-[4-amidinophenyl]aminomethyl]benzimidazol-5-yl-carboxylic acid-N-(2-pyridyl)-N-(2-ethoxycarbonylethyl)amide mesylate (25 g) at the same temperature. The reaction mixture was stirred at same temperature for 15-20 min and to this n-hexylchloroformate (8.9 gm) dissolved in acetone (10 ml) was added over a period of 10-15 min at the same temperature. The mixture was stirred at 15-20° C. for 1 hour. The completion of reaction was monitored by TLC. After the completion of reaction, the reaction mixture was diluted with water (125 ml) and the slurry was stirred for 1 hour at 15 to 20° C. The slurry was filtered and the solid was washed with water (2×50 ml) and dried at 40-45° C. to obtain Dabigatran etexilate tetrahydrate. Yield: 20 g (77%); Purity: greater than 97%

Example 6: Purification of Dabigatran Etexilate

In a 1 liter RB flask equipped with a mechanical stirrer, ethyl acetate (50 ml) and Dabigatran etexilate tetrahydrate (25 g) were charged at ambient temperature. Cyclohexane (175 ml) was charged at the same temperature and the resultant slurry was heated to 60-65° C. The slurry was stirred for 1 hour at the same temperature. The slurry was cooled to 20-25° C. and further stirred for 2 hours. The slurry was filtered and the solid obtained was washed with cyclohexane-ethyl acetate and dried at 40-45° C. for 2-3 hours to obtain pure Dabigatran etexilate tetrahydrate.
Yield: 20 g; Purity: greater than 97%

Example 7: Preparation of Dabigatran Etexilate Mesylate

In a 250 ml RB flask equipped with a mechanical stirrer and addition funnel, acetone (50 ml) and Dabigatran etexilate (5 gm) were charged at 25-30° C. The mixture was warmed to 40-45° C. to obtain a clear solution. The solution was cooled to 25-30° C. A solution of methane sulfonic acid (0.5 gm) in acetone (5 ml) was added to the above mixture over a period of 5-10 min. This mixture was stirred at 25-30° C. for 4 hours. The obtained slurry was filtered. The solid was washed with acetone (2×10 ml) and dried at 40° C. to obtain Dabigatran etexilate mesylate. Yield: 4.5 g; Purity: 99.7%.

Example 8: Preparation of Dabigatran Etexilate Anhydrous Form I

In a 500 ml RB flask equipped with a mechanical stirrer and addition funnel, ethyl acetate (200 ml) and Dabigatran etexilate tetrahydrate (20 g) were charged at ambient temperature. The mixture was heated to 65-70° C. to obtain a clear solution.
The solution was stirred for 10 to 15 min and then cooled to 25-30° C. The solution was stirred for 4 hours to obtain a slurry. The slurry was filtered and the solid obtained was washed with ethyl acetate (2×20 ml) and dried at 40-45° C. to obtain Dabigatran etexilate anhydrous Form I. Yield: 16 g; Purity: greater than 99%

Example 9: Preparation of Dabigatran Etexilate Mesylate Form I

In a 500 ml RB flask equipped with a mechanical stirrer and addition funnel, acetone (150 ml) and Dabigatran etexilate anhydrous Form I (15 g) were charged at ambient temperature. The mixture was warmed to 40-45° C. to obtain a clear solution. The solution was cooled to 25-30° C. and to this, a solution of methane sulfonic acid (2.3 g) in acetone (10 ml) was added over a period of 5-10 min. This mixture was maintained under stirring at 28-35° C. for 1 hour. The mixture was further cooled and maintained under stirring for 1 hour to obtain a slurry. The obtained slurry was filtered and the solid obtained was washed with acetone (2×15 ml) and dried at 40° C. to obtain Dabigatran etexilate mesylate Form I. Yield: 15 g; Purity: greater than 99.5%.

Example 10: Preparation of Dabigatran Etexilate Mesylate Form I

A solution of methane sulfonic acid (1.6 g) in ethyl acetate (100 ml) was taken in a 500 ml RB flask equipped with a mechanical stirrer and addition funnel. The temperature of the solution was maintained at 55° C. Dabigatran etexilate tetrahydrate (10 g) in ethyl acetate (200 ml) was taken in another RB flask and the mixture was heated at 55-60° C. to obtain a solution. The warm solution was filtered and the filtrate was added to the solution of methane sulfonic acid at 55° C. The mixture was maintained at the same temperature for 30 minutes. The solid separated is filtered and dried to obtain Dabigatran etexilate mesylate Form I. Yield: 9.5 g Example 11: Preparation of Dabigatran Etexilate (4-amidinophenyl)glycine ethyl ester (50 gm) was added in THF (600 ml) to obtain a mixture. To this mixture, water (200 ml) was added followed by addition of a base (62.4 gm) and the mass was cooled to 15-20° C. To this mixture, n-hexylchloroformate (40.5 gm) was added dropwise. The temperature of the reaction mass was raised to room temperature and was maintained under stirring at the same temperature for 2 hours. The completion of the reaction was monitored by TLC. The layers were separated and the aqueous layer was extracted with THF (250 ml). The organic layer was concentrated under vacuum. The oil obtained was treated with dichloromethane and water. The organic layer was washed with water and distilled at 40° C. to obtain a residue. To this residue, hexane (500 ml) was added and the mixture was stirred at room temperature. The solid separated was filtered, washed with hexane (250 ml) and dried at 50-55° C. to obtain 50 gm of [(4-{[(hexyloxy)carbonyl]carbamimidoyl}phenyl)amino]acetic acid ethyl ester. Yield: 63.1%

[(4-{[(hexyloxy)carbonyl]carbamimidoyl}phenyl)amino]acetic acid ethyl ester (50 gm), ethanol (500 ml) and water (150 ml) were stirred at room temperature to obtain a mixture. To this mixture, was added lithium hydroxide monohydrate (7.17 gm) and the obtained mixture was stirred for 2 hours. The completion of the reaction was monitored by TLC. The pH of the reaction mass was adjusted to 5-6 using hydrochloric acid (approx. 17%). This reaction mass was stirred at room temperature for 2 hours and the separated solid was filtered, washed with THF (150 ml) and dried at 50-60° C. to obtain 32 gm of [(4-{[(hexyloxy)carbonyl]carbamimidoyl}phenyl)amino]acetic acid. Yield: 70%

To a 100 ml flask, THF (20 ml), [(4-{[(hexyloxy)carbonyl]carbamimidoyl}phenyl)amino]acetic acid (1 gm) and Ethyl-3-[-(3-amino-4-methylaminobenzoyl)-(pyridin-2-yl)-amino]propanoate (0.96 gm) were charged at room temperature. To this mixture, N-methyl pyrrolidine (1.1 ml) and EDC-HCl (1.8 gm) was charged and this mixture was refluxed for 1 hour. The completion of the reaction was monitored by TLC. The reaction mixture was concentrated to get a residue. This residue was diluted with water (10 ml) and dichloromethane (20 ml) and the obtained mixture was stirred for 5 mins. The organic layer was separated and concentrated to get 2.8 gm of the crude material. The crude product was purified by column chromatography to get 0.73 gm of the pure product.

We claim:

1. A process for preparation of Dabigatran etexilate or pharmaceutically acceptable salt thereof, comprising the steps of, a) treating Ethyl-3-{[(2-formyl-1-methyl-1H-benzimidazole-5-yl)carbonyl]-(2-pyridinyl)amino}propanoate with 4-aminobenzamidine or N-hydroxy-4-aminobenzamidine in presence of a reducing agent to obtain 1-methyl-2-[N-[4-amidinophenyl]aminomethyl]-benzimidazol-5-yl-carboxylic acid-N-(2-pyridyl)-N-(2-ethoxycarbonyl ethyl)amide;
   b) optionally purifying said 1-methyl-2-[N-[4-amidinophenyl]aminomethyl]-benzimidazol-5-yl-carboxylic acid-N-(2-pyridyl)-N-(2-ethoxy carbonyl ethyl)amide;
   c) converting said 1-methyl-2-[N-[4-amidinophenyl]aminomethyl]benzimidazol-5-yl-carboxylic acid-N-(2-pyridyl)-N-(2-ethoxycarbonyl ethyl)amide to Dabigatran etexilate or pharmaceutically acceptable salt thereof.

2. The process as claimed in claim 1, wherein said reaction in step a) is carried out at a temperature of about 10° C. to 20° C.

3. The process as claimed in claim 2, wherein said reaction is carried out in the presence of a reducing agent selected from sodium borohydride, sodium cyanoborohydride, sodium triacetoxy borohydride, lithium borohydride, lithium aluminium hydride or diisobutylaluminium hydride; and solvent selected from acetic acid, formic acid, ethanol, methanol, isopropanol, n-propanol, n-butanol or mixture thereof and wherein said purification of 1-methyl-2-[N-[4-amidinophenyl]aminomethyl]-benzimidazol-5-yl-carboxylic acid-N-(2-pyridyl)-N-(2-ethoxy carbonyl ethyl)amide is carried out by conversion to its acid addition salt.

4. The process as claimed in claim 1, said process further comprising the steps of, a) treating Ethyl-3-[(3-amino-4-methylaminobenzoyl)-N-(pyridin-2-yl)-amino]propanoate with an acetic acid derivative to obtain Ethyl-3-{[(2-dichloromethyl-1-methyl-1H-benzimidazole-5-yl)carbonyl]-(2-pyridinyl)amino}propanoate;
   b) converting Ethyl-3-{[(2-dichloromethyl-1-methyl-1H-benzimidazole-5-yl)carbonyl]-(2-pyridinyl)amino}propanoate to Ethyl-3-{[(2-formyl-1-methyl-1H-benzimidazole-5-yl)carbonyl]-(2-pyridinyl)amino}propanoate, either by
      i. treating Ethyl-3-{[(2-dichloromethyl-1-methyl-1H-benzimidazole-5-yl) carbonyl]-(2-pyridinyl)amino}propanoate with an acetate forming agent in the presence of phase transfer catalyst to form the diacetate compound;
      ii. treating the diacetate compound with a base at a temperature of at least about 35° C. to obtain Ethyl-3-{[(2-formyl-1-methyl-1H-benzimidazole-5-yl) carbonyl]-(2-pyridinyl)amino}propanoate
      OR
      i. reacting Ethyl-3-{[(2-dichloromethyl-1-methyl-1H-benzimidazole-5-yl) carbonyl]-(2-pyridinyl)amino}propanoate with DMSO-base or sodium metaperiodate-DMF to obtain Ethyl-3-{[(2-formyl-1-methyl-1H-benzimidazole-5-yl)carbonyl]-(2-pyridinyl)amino}propanoate;
      ii. isolating Ethyl-3-{[(2-formyl-1-methyl-1H-benzimidazole-5-yl)carbonyl]-(2-pyridinyl)amino}propanoate;
   wherein said acetic acid derivative is selected from the group consisting of dichloroacetyl chloride, dichloroacetic anhydride, and dichloroacetic acid.

5. The process as claimed in claim 4, wherein said treatment in step a) is carried out at a temperature of about 40° C.-80° C. in presence of solvent selected from acetonitrile, THF, chlorobenzene, ethyl acetate, methyl acetate or butyl acetate and wherein said acetate forming agent is sodium acetate or potassium acetate and said phase transfer catalyst is a quaternary ammonium salt.

6. The process as claimed in claim 1, said process further comprising the steps of,
   a) treating Ethyl-3-[(3-amino-4-methylaminobenzoyl)-N-(pyridin-2-yl)-amino]propanoate with an acetic acid derivative in presence of solvent selected from toluene, xylene, heptane, cyclohexane, dichloromethane, dichloroethane or methyl tert butyl ether at reflux temperature to obtain Ethyl-3-{[(2-hydroxymethyl-1-methyl-1H-benzimidazole-5-yl)carbonyl]-(2-pyridinyl)amino}propanoate;
   b) treating Ethyl-3-{[(2-hydroxymethyl-1-methyl-1H-benzimidazole-5-yl)carbonyl]-(2-pyridinyl) amino}propanoate with oxidizing agent to obtain Ethyl-3-{[(2-formyl-1-methyl-1H-benzimidazole-5-yl)carbonyl]-(2-pyridinyl)amino}propanoate; wherein said acetic acid derivative is glycolic acid.

7. The process as claimed in claim 1, said process further comprising the steps of,
   a) treating Ethyl-3-[(3-amino-4-methylaminobenzoyl)-N-(pyridin-2-yl)-amino]propanoate with an acetic acid derivative to obtain Ethyl-3-{[(1,2-dimethyl-1H-benzimidazol-5-yl)carbonyl]-(2-pyridinyl) amino}propanoate;
   b) optionally, treating Ethyl-3-{[(1,2-dimethyl-1H-benzimidazol-5-yl)carbonyl]-(2-pyridinyl) amino}propanoate with a halogenating agent to obtain Ethyl-3-{[(2-dihalomethyl-1-methyl-1-methyl-1H-benzimidazole-5-yl)carbonyl]-(2-pyridinyl) amino}propanoate;
   c) treating said Ethyl-3-{[(1,2-dimethyl-1H-benzimidazol-5-yl)carbonyl]-(2-pyridinyl) amino}propanoate or said Ethyl-3-{[(2-dihalomethyl-1-methyl-1H-benzimidazole-5-yl)carbonyl]-(2-pyridinyl)amino}propanoate with oxidizing agent to obtain Ethyl-3-{[(2-formyl-1-methyl-1H-benzimidazole-5-yl)carbonyl]-(2-pyridinyl)amino}propanoate;
   wherein said acetic acid derivative is selected from the group consisting of acetic acid, acetic anhydride, acetyl chloride, and acetyl bromide.

8. The process as claimed in claim 7, wherein said oxidizing agent is selected from selenium dioxide, chromyl chloride, chromium trioxide, potassium permanganate, manganese dioxide, ceric ammonium nitrate, ceric trifluoroacetate, pyridinium chlorochromate, silver oxide or Bromine-DMSO and wherein said halogenating agent is selected from N-halosuccinimide, chlorine, bromine, hypochlorite or hypobromite.

9. The process as claimed in claim 1, said process further comprising treating Ethyl-3-[(3-amino-4-methylaminobenzoyl)-N-(pyridin-2-yl)-amino]propanoate with an acetic acid derivative to obtain Ethyl-3-{[(2-formyl-1-methyl-1H-benzimidazole-5-yl) carbonyl]-(2-pyridinyl) amino}propanoate, wherein said acetic acid derivative is glyoxylic acid.

10. The process as claimed in claim 1, wherein said 1-methyl-2-[N-[4-amidinophenyl]aminomethyl]-benzimidazol-5-yl-carboxylic acid-N-(2-pyridyl)-N-(2-ethoxy carbonylethyl)amide is purified by conversion to its mesylate salt and said conversion of 1-methyl-2-[N-[4-amidinophenyl]aminomethyl]benzimidazol-5-yl-carboxylic acid-N-(2-pyridyl)-N-(2-ethoxycarbonyl ethyl)amide to Dabigatran etexilate or pharmaceutically acceptable salt thereof comprises treating said 1-methyl-2-[N-[4-amidino phenyl]aminomethyl]benzimidazol-5-yl-carboxylic acid-N-(2-pyridyl)-N-(2-ethoxycarbonyl ethyl)amide or salt thereof with n-hexyl chloroformate to obtain Dabigatran etexilate or pharmaceutically acceptable salt thereof.

11. A compound of formula II

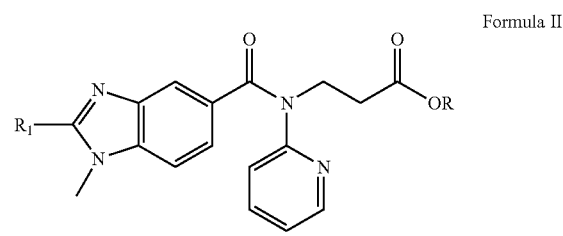

Formula II wherein R=–H or $C_1$-$C_5$ alkyl;
and R=—CHO or —$CH_3$, or —$CHX_2$, where X=—Cl, —Br, —I.

12. The compound as claimed in claim 11, wherein
when $R_1$=—CHO, R=—H, —$CH_3$ or —$C_2H_5$;
when $R_1$=—$CHCl_2$, R=–H, —$CH_3$ or —$C_2H_5$; or
when R=—$CH_3$, R=—H, —$CH_3$ or —$C_2H_5$.

13. The compound as claimed in claim 12, wherein the compound is selected from the group consisting of,
Ethyl-3-{[(2-dichloromethyl-1-methyl-1H-benzimidazole-5-yl)carbonyl]-(2-pyridinyl)amino}propanoate; Ethyl-3-{[(2-formyl-1-methyl-1H-benzimidazole-5-yl)carbonyl]-(2-pyridinyl)amino}propanoate; 3-{[(2-dichloromethyl-1-methyl-1H-benzimidazole-5-yl)carbonyl]-(2-pyridinyl)amino}propanoic acid and 3-{[(2-formyl-1-methyl-1H-benzimidazole-5-yl)carbonyl]-(2-pyridinyl)amino}propanoic acid.

14. The compound as claimed in claim 12, wherein the compound is selected from the group consisting of,
Methyl-3-{[(2-dichloromethyl-1-methyl-1H-benzimidazole-5-yl)carbonyl]-(2-pyridinyl)amino}propanoate; Methyl-3-{([(2-formyl-1-methyl-1H-benzimidazole-5-yl)carbonyl]-(2-pyridinyl)amino}propanoate; Ethyl-3-{[1,2-dimethyl-1H-benzimidazol-5-yl)carbonyl]-(2-pyridinyl)amino}propanoate; Methyl-3-{[(1,2-dimethyl-1H-benzimidazol-5-yl) carbonyl]-(2-pyridinyl)amino}propanoate and 3-{[(1,2-dimethyl-1H-benzimidazol-5-yl)carbonyl]-(2-pyridinyl) amino}propanoic acid.

15. A process for preparation of compound of Formula II as defined in claim 11, where R1=—CHO, R=—H or —$C_2H_5$, wherein the process comprises reacting 2-formyl-1-methyl-1H-benzimidazole-5-carboxylic acid with 3-[N-(2-pyridinyl)-amino]propanoic acid or ethyl ester thereof in presence of a halogenating agent selected from thionyl chloride, phosphorus trichloride or phosphorus pentachloride to obtain 3-{[(2-formyl-1-methyl-1H-benzimidazole-5-yl)carbonyl]-(2-pyridinyl)amino}propanoic acid or ethyl ester thereof.

16. The process as claimed in claim 15, wherein said 2-formyl-1-methyl-1H-benzimidazole-5-carboxylic acid is prepared by a process comprising the steps of,
   a) treating 3-amino-4-(methylamino)benzoic acid or esters thereof with dihaloacetyl halide, dihaloacetic anhydride or dihaloacetic acid to obtain 2-(dihalomethyl)-1-methyl-1H-benzimidazole-5-carboxylic acid or ester thereof;
   b) treating 2-(dihalomethyl)-1-methyl-1H-benzimidazole-5-carboxylic acid or ester thereof with DMSO-base or sodium metaperiodate-DMF to obtain 2-formyl-1-methyl-1H-benzimidazole-5-carboxylic acid;
OR
a) treating 3-amino-4-(methylamino)benzoic acid or esters thereof with glycolic acid to obtain 2-hydroxymethyl-1-methyl-1H-benzimidazole-5-carboxylic acid or ester thereof;
b) subjecting 2-hydroxymethyl-1-methyl-1H-benzimidazole-5-carboxylic acid or ester thereof to oxidation using manganese dioxide, Dess-Martin periodinane or pyridinium chloroformate to obtain 2-formyl-1-methyl-1H-benzimidazole-5-carboxylic acid;
OR
a) treating 3-amino-4-(methylamino) benzoic acid or esters thereof with acetic acid, acetic anhydride, acetyl chloride or acetyl bromide to obtain 1,2-dimethyl-1H-benzimidazole-5-carboxylic acid or ester thereof; and
b) subjecting 1,2-dimethyl-1H-benzimidazole-5-carboxylic acid or ester thereof to oxidation using manganese dioxide, Dess-Martin periodinane or pyridinium chloroformate to obtain 2-formyl-1-methyl-1H-benzimidazole-5-carboxylic acid;
OR
treating 3-amino-4-(methylamino) benzoic acid or ester thereof with glyoxylic acid to obtain 2-formyl-1-methyl-1H-benzimidazole-5-carboxylic acid.

17. The process as claimed in claim 1, wherein said Dabigatran etexilate is converted to Dabigatran etexilate mesylate, by a process comprising,
   a) treating Dabigatran etexilate in a solvent selected from acetone, acetonitrile, tetrahydrofuran, ethyl acetate, methyl acetate, dimethyl formamide, dimethyl acetamide or dimethyl sulfoxide to obtain a solution;
   b) treating the solution of step a) with methane sulfonic acid to obtain a mixture; and
   c) isolating Dabigatran etexilate mesylate Form I from said mixture.

18. The process as claimed in claim 17, wherein said Dabigatran etexilate is Dabigatran etexilate anhydrous Form I or Dabigatran etexilate tetrahydrate.

19. The process as claimed in claim 1, wherein said Dabigatran etexilate obtained is tetrahydrate and wherein said conversion to Dabigatran etexilate mesylate comprises the steps of,
   a) obtaining a solution of Dabigatran etexilate tetrahydrate;
   b) adding the obtained solution to a solution of methanesulfonic acid to obtain a mixture; and
   c) isolating Dabigatran etexilate mesylate Form I from said mixture.

20. The process as claimed in claim 6, wherein said oxidizing agent is selected from manganese dioxide, Dess-Martin periodinane or pyridinium chlorochromate.

21. The process as claimed in claim 1, wherein reduction is carried out in the presence of a catalyst selected from palladium/carbon, platinum/carbon or oxides thereof supported on carbon or alumina.

22. A process for preparation of Dabigatran etexilate or pharmaceutically acceptable salt thereof, comprising the steps of,
   a) converting a compound of Formula II

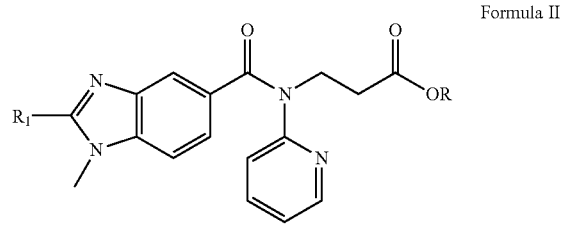

Formula II wherein $R_1$ is $CH_3$ or $-CHX_2$, where X is $-Cl$, $-Br$, or $-I$ and R is $-H$, $-CH_3$ or $-C_2H_5$, to a compound of Formula II, wherein $R_1$ is $-CHO$ and R is $-H$, $-CH_3$ or $-C_2H_5$;
   b) converting said compound of Formula II, wherein $R_1$ is $-CHO$ and R is $-H$, $-CH_3$ or $-C_2H_5$ to 1-methyl-2-[N-[4-amidinophenyl]aminomethyl]-benzimidazol-5-yl-carboxylic acid-N-(2-pyridyl)-N-(2-ethoxycarbonyl ethyl)amide; and
   c) converting said 1-methyl-2-[N-[4-amidinophenyl]aminomethyl]-benzimidazol-5-yl-carboxylic acid-N-(2-pyridyl)-N-(2-ethoxycarbonyl ethyl)amide to Dabigatran etexilate or a pharmaceutically acceptable salt thereof.

23. The process as claimed in claim 22, wherein said compound of Formula II, wherein $R_1$ is $-CH_3$, or $-CHX_2$, where X is $-Cl$, $-Br$, or $-I$, is selected from the group consisting of Ethyl-3-{[(1,2-dimethyl-1H-benzimidazol-5-yl)carbonyl]-(2-pyridinyl)propanoate, Methyl-3-{[(1,2-dimethyl-1H-benzimidazol-5-yl)carbonyl]-(2-pyridinyl)amino}propanoate, 3-{[(1,2-dimethyl-1H-benzimidazol-5-yl)carbonyl]-(2-pyridinyl)amino}propanoic acid, Ethyl-3-{[(2-dichloromethyl-1-methyl-1H-benzimidazole-5-yl)carbonyl]-(2-pyridinyl) amino}propanoate, 3-{[(2-dichloromethyl-1-methyl-1H-benzimidazole-5-yl)carbonyl]-(2-pyridinyl)amino}propanoic acid, and Methyl-3-{[(2-dichloromethyl-1-methyl-1H-benzimidazole-5-yl) carbonyl]-(2-pyridinyl)amino}propanoate.

24. The process as claimed in claim 22, wherein said compound of Formula II, wherein $R_1$ is $-CHO$, is selected from the group consisting of Ethyl-3-{[(2-formyl-1-methyl-1H-benzimidazole-5-yl)carbonyl]-(2-pyridinyl) amino}propanoate, 3-{[(2-formyl-1-methyl-1H-benzimidazole-5-yl)carbonyl]-(2-pyridinyl)amino}propanoic acid, and Methyl-3-{[(2-formyl-1-methyl-1H-benzimidazole-5-yl)carbonyl]-(2-pyridinyl)amino}propanoate.

* * * * *

UNITED STATES PATENT AND TRADEMARK OFFICE
CERTIFICATE OF CORRECTION

| | | |
|---|---|---|
| PATENT NO. | : 9,688,657 B2 | Page 1 of 1 |
| APPLICATION NO. | : 14/779911 | |
| DATED | : June 27, 2017 | |
| INVENTOR(S) | : Patkar et al. | |

It is certified that error appears in the above-identified patent and that said Letters Patent is hereby corrected as shown below:

In the Claims

In Column 37, Line 30-32, in Claim 7, delete "Ethyl-3-{[(2-dihalomethyl-1-methyl-1-methyl-1H-benzimidazole-5-yl)carbonyl]-(2-pyridinyl)amino}propanoate;" and insert --Ethyl-3-{[(2-dihalomethyl-1-methyl-1H-benzimidazole-5-yl)carbonyl]-(2-pyridinyl)amino}propanoate;-- therefor In Column 38, Line 18, in Claim 11, delete "R=-CHO" and insert --$R_1$=-CHO-- therefor In Column 38, Line 23, in Claim 12, delete "R=-$CH_3$," and insert --$R_1$=-$CH_3$,-- therefor In Column 38, Line 39-40, in Claim 14, delete "Methyl-3-{([(2-formyl-1-methyl-1H-benzimidazole-5-yl)carbonyl]-(2-pyridinyl)amino}propanoate;" and insert --Methyl-3-{[(2-formyl-1-methyl-1H-benzimidazole-5-yl)carbonyl]-(2-pyridinyl)amino}propanoate;-- therefor In Column 38, Line 49, in Claim 15, delete "R1=-CHO," and insert --$R_1$=-CHO,-- therefor <div style="text-align:right">

Signed and Sealed this
Thirty-first Day of July, 2018

Andrei Iancu
*Director of the United States Patent and Trademark Office*

</div>